US011399755B2

United States Patent
Ivosevic et al.

(10) Patent No.: US 11,399,755 B2
(45) Date of Patent: Aug. 2, 2022

(54) DEVICE FOR OBTAINING A BLOOD SAMPLE

(71) Applicant: Becton, Dickinson and Company, Franklin Lakes, NJ (US)

(72) Inventors: Milan Ivosevic, Kinnelon, NJ (US); Jayeon Kim, River Edge, NJ (US); Kishore K. Bokka Srinivasa Rao, Ridgewood, NJ (US); Michel Bruehwiler, Franklin Lakes, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 505 days.

(21) Appl. No.: 16/327,100

(22) PCT Filed: Aug. 23, 2017

(86) PCT No.: PCT/US2017/048143
§ 371 (c)(1),
(2) Date: Feb. 21, 2019

(87) PCT Pub. No.: WO2018/039305
PCT Pub. Date: Mar. 1, 2018

(65) Prior Publication Data
US 2019/0216380 A1   Jul. 18, 2019

Related U.S. Application Data

(60) Provisional application No. 62/378,971, filed on Aug. 24, 2016.

(51) Int. Cl.
*A61B 5/15* (2006.01)

(52) U.S. Cl.
CPC .. *A61B 5/150389* (2013.01); *A61B 5/150022* (2013.01); *A61B 5/15045* (2013.01); *A61B 5/150068* (2013.01); *A61B 5/150106* (2013.01); *A61B 5/150251* (2013.01); *A61B 5/150259* (2013.01); *A61B 5/150343* (2013.01); *A61B 5/150404* (2013.01); *A61B 5/150755* (2013.01)

(58) Field of Classification Search
CPC ........ A61B 5/150343; A61B 5/150068; A61B 5/150389; A61B 5/150022
See application file for complete search history.

(56) References Cited

U.S. PATENT DOCUMENTS

| 2,646,799 A | 7/1953 | Jacoby, Jr. |
| 3,623,475 A | 11/1971 | Sanz et al. |
| 3,626,929 A | 12/1971 | Sanz et al. |

(Continued)

FOREIGN PATENT DOCUMENTS

| DE | 10315396 A1 | 10/2004 |
| EP | 0224650 A2 | 6/1987 |

(Continued)

*Primary Examiner* — Eric F Winakur
(74) *Attorney, Agent, or Firm* — The Webb Law Firm

(57) ABSTRACT

A device for obtaining a biological sample, such as a capillary blood collection device, that has the ability to lance and squeeze the finger, collect the sample, stabilize the sample, and subsequently dispense the sample in a controlled manner is disclosed. The device also simplifies and streamlines the capillary blood collection by eliminating workflow variabilities which are typically associated with low sample quality including hemolysis and micro-clots.

29 Claims, 22 Drawing Sheets

(56) References Cited

U.S. PATENT DOCUMENTS

| | | |
|---|---|---|
| 3,630,191 A | 12/1971 | Gilford |
| 3,741,197 A | 6/1973 | Sanz et al. |
| 4,024,857 A | 5/1977 | Blecher et al. |
| 4,397,318 A | 8/1983 | Burns |
| 4,411,163 A | 10/1983 | White |
| 4,620,549 A | 11/1986 | Nugent |
| 4,690,153 A | 9/1987 | Losada et al. |
| 4,805,635 A | 2/1989 | Korf et al. |
| 5,014,718 A | 5/1991 | Mitchen |
| 5,038,794 A | 8/1991 | Van Valkenburg |
| 5,070,886 A | 12/1991 | Mitchen et al. |
| 5,181,523 A | 1/1993 | Wendelborn |
| 5,384,096 A | 1/1995 | Burns |
| 5,458,854 A | 10/1995 | Burns |
| 5,485,856 A | 1/1996 | Buckland |
| 5,569,223 A | 10/1996 | Wandell et al. |
| 5,624,458 A | 4/1997 | Lipscher |
| 5,662,127 A | 9/1997 | De Vaughn |
| 5,709,699 A | 1/1998 | Warner |
| 5,843,112 A | 12/1998 | De Vaughn |
| 5,857,983 A | 1/1999 | Douglas et al. |
| 5,891,053 A | 4/1999 | Sesekura |
| 5,951,492 A | 9/1999 | Douglas et al. |
| 5,951,493 A | 9/1999 | Douglas et al. |
| 6,048,352 A | 4/2000 | Douglas et al. |
| 6,071,250 A | 6/2000 | Douglas et al. |
| 6,319,210 B1 | 11/2001 | Douglas et al. |
| 6,352,514 B1 | 3/2002 | Douglas et al. |
| 6,485,439 B1 | 11/2002 | Roe et al. |
| 6,503,210 B1 | 1/2003 | Hirao et al. |
| 6,551,267 B1 | 4/2003 | Cohen et al. |
| 6,589,260 B1 | 7/2003 | Schmelzeisen-Redeker et al. |
| 6,626,851 B2 | 9/2003 | Hirao et al. |
| 6,679,852 B1 | 1/2004 | Schmelzeisen-Redeker et al. |
| 6,706,000 B2 | 3/2004 | Perez et al. |
| 6,706,049 B2 | 3/2004 | Moerman |
| D488,232 S | 4/2004 | Nan |
| D488,588 S | 4/2004 | Murphy |
| 7,131,984 B2 | 11/2006 | Sato et al. |
| 7,201,723 B2 | 4/2007 | Chan |
| 7,291,159 B2 | 11/2007 | Schmelzeisen-Redeker et al. |
| D569,514 S | 5/2008 | Poll et al. |
| 7,384,402 B2 | 6/2008 | Wong et al. |
| D576,277 S | 9/2008 | Oren et al. |
| D582,037 S | 12/2008 | Poll et al. |
| 7,591,791 B2 | 9/2009 | Keren |
| 7,727,168 B2 | 6/2010 | Douglas et al. |
| 7,731,668 B2 | 6/2010 | Douglas et al. |
| 7,758,516 B2 | 7/2010 | Perez |
| 7,758,518 B2 | 7/2010 | Perez et al. |
| 7,758,602 B2 | 7/2010 | Sato et al. |
| 7,841,991 B2 | 11/2010 | Douglas et al. |
| 8,062,274 B2 | 11/2011 | Rasch-Menges et al. |
| 8,360,993 B2 | 1/2013 | Escutia et al. |
| 8,372,015 B2 | 2/2013 | Escutia et al. |
| 8,376,959 B2 | 2/2013 | Deck |
| 8,475,395 B2 | 7/2013 | Nakayama et al. |
| 8,523,894 B2 | 9/2013 | Schmelzeisen-Redeker et al. |
| 8,636,674 B2 | 1/2014 | Roe |
| 8,684,949 B2 | 4/2014 | Hoenes et al. |
| 8,690,798 B2 | 4/2014 | Douglas et al. |
| D707,364 S | 6/2014 | Spencer |
| 8,740,813 B2 | 6/2014 | Douglas et al. |
| 8,858,467 B2 | 10/2014 | List et al. |
| 8,926,644 B2 | 1/2015 | Schiff et al. |
| 8,956,307 B2 | 2/2015 | Morita et al. |
| D732,684 S | 6/2015 | Ooi et al. |
| D742,005 S | 10/2015 | Komuda et al. |
| 9,226,704 B2 | 1/2016 | Deck |
| 9,289,763 B2 | 3/2016 | Berthier et al. |
| 9,295,416 B2 | 3/2016 | Bartfeld et al. |
| D757,267 S | 5/2016 | Shi |
| 9,326,718 B2 | 5/2016 | Petrich et al. |
| 9,332,931 B2 | 5/2016 | Chan |
| 9,380,963 B2 | 7/2016 | Gofman et al. |
| 9,380,970 B2 | 7/2016 | Christensen et al. |
| 9,380,975 B2 | 7/2016 | Karbowniczek et al. |
| 9,414,774 B2 | 8/2016 | Korner et al. |
| 9,427,184 B2 | 8/2016 | Holmes et al. |
| 9,456,782 B2 | 10/2016 | Rasch-Menges et al. |
| 9,538,941 B2 | 1/2017 | Perez et al. |
| 9,554,741 B2 | 1/2017 | Roe et al. |
| 9,556,027 B2 | 1/2017 | Chakravarti et al. |
| 9,566,027 B2 | 2/2017 | Tamir |
| 9,681,834 B2 | 6/2017 | Suess |
| D800,333 S | 10/2017 | Snider et al. |
| 9,833,183 B2 | 12/2017 | Escutia et al. |
| 9,849,251 B2 | 12/2017 | Crawford et al. |
| 10,093,918 B2 | 10/2018 | Mielke et al. |
| 10,126,211 B2 | 11/2018 | Yamakawa et al. |
| 10,136,848 B2 | 11/2018 | Hsiung et al. |
| 10,251,589 B2 | 4/2019 | Korner et al. |
| D856,148 S | 8/2019 | Lucas, Jr. et al. |
| D868,269 S | 11/2019 | Sayre |
| D881,410 S | 4/2020 | Motadel et al. |
| D882,113 S | 4/2020 | Motadel et al. |
| 10,610,142 B1 | 4/2020 | Diju et al. |
| 10,631,771 B2 | 4/2020 | Naghavi et al. |
| 10,722,163 B2 | 7/2020 | McHale et al. |
| 2003/0195540 A1 | 10/2003 | Moerman |
| 2004/0092843 A1 | 5/2004 | Kreiser et al. |
| 2004/0127818 A1 | 7/2004 | Roe et al. |
| 2005/0215923 A1 | 9/2005 | Wiegel |
| 2005/0234486 A1 | 10/2005 | Allen et al. |
| 2005/0234489 A1 | 10/2005 | Allen |
| 2005/0234491 A1 | 10/2005 | Allen et al. |
| 2005/0277849 A1 | 12/2005 | Wong et al. |
| 2006/0052809 A1 | 3/2006 | Karbowniczek et al. |
| 2007/0060842 A1 | 3/2007 | Alvarez-Icaza et al. |
| 2007/0060843 A1 | 3/2007 | Alvarez-Icaza et al. |
| 2007/0060844 A1 | 3/2007 | Alvarez-Icaza et al. |
| 2007/0073187 A1 | 3/2007 | Thomson et al. |
| 2007/0073191 A1 | 3/2007 | Thomson et al. |
| 2007/0083130 A1 | 4/2007 | Thomson et al. |
| 2007/0083131 A1 | 4/2007 | Escutia et al. |
| 2007/0093863 A1 | 4/2007 | Pugh |
| 2007/0093864 A1 | 4/2007 | Pugh |
| 2007/0112281 A1 | 5/2007 | Olson |
| 2007/0112367 A1 | 5/2007 | Olson |
| 2007/0156065 A1 | 7/2007 | Chan |
| 2008/0294064 A1 | 11/2008 | Calasso et al. |
| 2009/0112121 A1 | 4/2009 | Chuang et al. |
| 2009/0112122 A1 | 4/2009 | Chuang et al. |
| 2009/0112125 A1* | 4/2009 | Tamir ............... A61B 5/15087 600/583 |
| 2009/0177224 A1 | 7/2009 | Naghavi et al. |
| 2009/0198152 A1 | 8/2009 | Kim |
| 2009/0259145 A1 | 10/2009 | Bartfeld et al. |
| 2009/0287117 A1 | 11/2009 | Harttig et al. |
| 2010/0010374 A1 | 1/2010 | Escutia et al. |
| 2010/0021947 A1* | 1/2010 | Emery ............... A61B 5/15163 435/14 |
| 2010/0036281 A1 | 2/2010 | Doi |
| 2010/0113981 A1 | 5/2010 | Oki et al. |
| 2010/0261988 A1 | 10/2010 | Tamir |
| 2011/0092854 A1 | 4/2011 | Kraemer et al. |
| 2011/0118568 A1 | 5/2011 | Sei |
| 2011/0270129 A1 | 11/2011 | Hoerauf |
| 2013/0211289 A1 | 8/2013 | Moga et al. |
| 2014/0318282 A1 | 10/2014 | Blekher et al. |
| 2015/0105813 A1 | 4/2015 | Li et al. |
| 2015/0351676 A1* | 12/2015 | Faurie ............... A61B 5/150305 600/583 |
| 2016/0174888 A1 | 6/2016 | Berthier et al. |
| 2016/0302708 A1 | 10/2016 | Christensen et al. |
| 2016/0367176 A1 | 12/2016 | Korner et al. |
| 2017/0020426 A1 | 1/2017 | Holmes et al. |
| 2017/0079569 A1 | 3/2017 | Rasch-Menges et al. |
| 2017/0122846 A1 | 5/2017 | Holmes et al. |
| 2017/0181682 A1 | 6/2017 | Tamir |
| 2018/0214059 A1 | 8/2018 | Escutia et al. |
| 2018/0220944 A1 | 8/2018 | Otsubo et al. |
| 2018/0303385 A1 | 10/2018 | Hatamian et al. |
| 2018/0306831 A1 | 10/2018 | Hatamian |

(56) References Cited

U.S. PATENT DOCUMENTS

| | | |
|---|---|---|
| 2019/0015030 A1 | 1/2019 | Barker |
| 2019/0099117 A1 | 4/2019 | Pulitzer et al. |
| 2019/0184100 A1 | 6/2019 | Fukuda et al. |
| 2019/0212345 A1 | 7/2019 | Lam et al. |
| 2019/0261961 A1 | 8/2019 | Esfandiari |
| 2019/0371136 A1 | 12/2019 | Whitaker |
| 2020/0054260 A1 | 2/2020 | Hatamian |
| 2021/0030346 A1 | 2/2021 | Noguchi et al. |

FOREIGN PATENT DOCUMENTS

| | | |
|---|---|---|
| EP | 0224650 B1 | 6/1992 |
| EP | 1157660 A1 | 11/2001 |
| EP | 1157660 B1 | 9/2007 |
| EP | 2184012 A1 | 5/2010 |
| EP | 2243427 B1 | 4/2013 |
| EP | 2184012 B1 | 6/2013 |
| GB | 2183159 A | 6/1987 |
| GB | 2409411 A | 6/2005 |
| JP | H04506024 A | 10/1992 |
| JP | 2002219115 A | 8/2002 |
| JP | 200594425 A | 4/2005 |
| JP | 2005131009 A | 5/2005 |
| JP | 2006043016 A | 2/2006 |
| JP | 2007111215 A | 5/2007 |
| JP | 2011078518 A | 4/2011 |
| JP | 4762341 B2 | 8/2011 |
| RU | 2580295 C2 | 7/2015 |
| RU | 2570750 C2 | 12/2015 |
| WO | 02100254 A2 | 12/2002 |
| WO | 2004064637 A1 | 8/2004 |
| WO | 2008027319 A2 | 3/2008 |
| WO | 2009081405 A2 | 7/2009 |
| WO | 2009095184 A1 | 8/2009 |
| WO | 2009145920 A1 | 12/2009 |
| WO | 2014063344 A1 | 5/2014 |
| WO | 2015191853 A1 | 12/2015 |
| WO | 2016161083 A1 | 10/2016 |
| WO | 2017221698 A1 | 12/2017 |
| WO | 2018160523 A1 | 9/2018 |
| WO | 2018218341 A1 | 12/2018 |
| WO | 2019220938 A1 | 11/2019 |
| WO | 2020047070 A1 | 3/2020 |

* cited by examiner

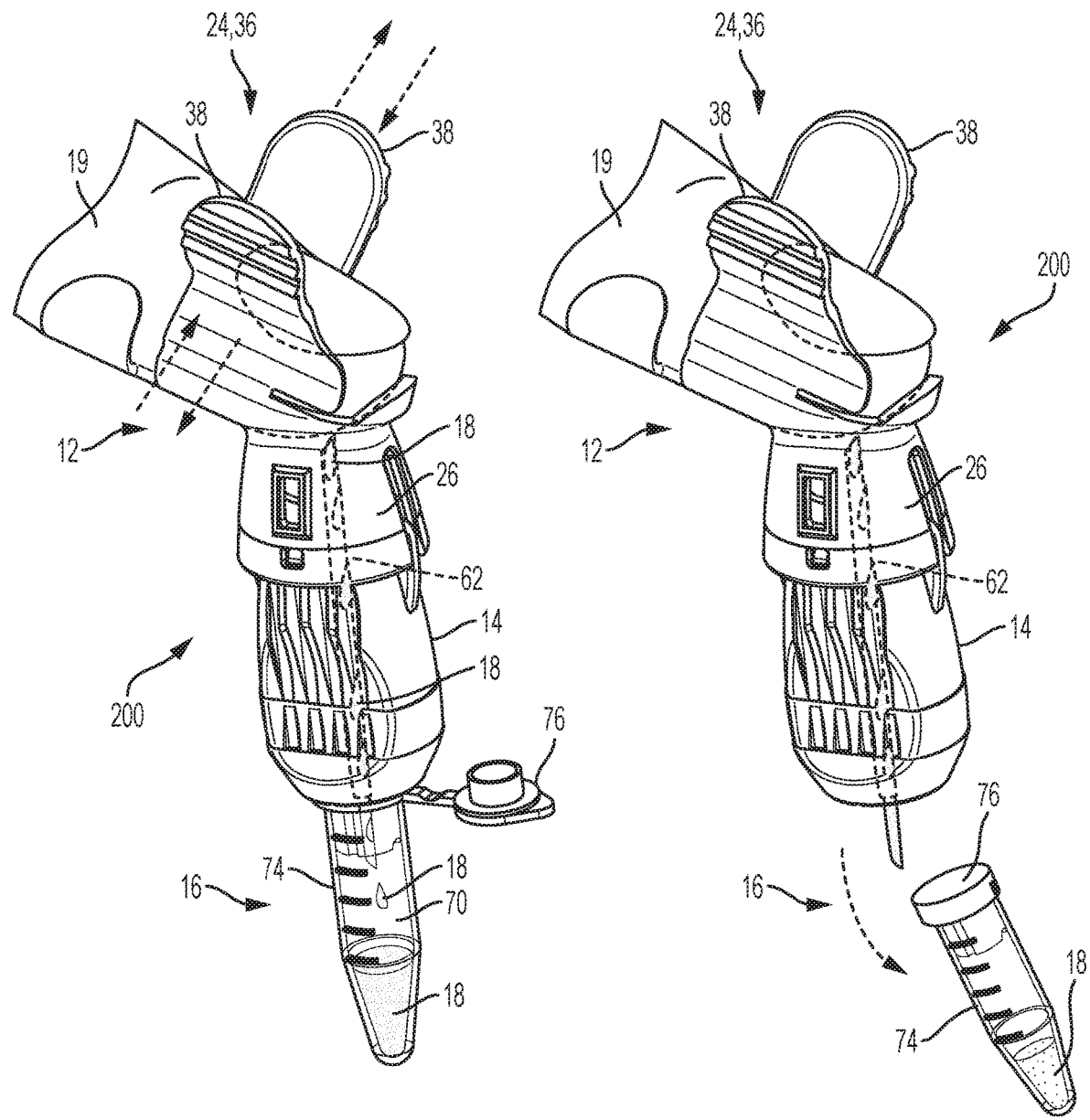

DEVICE FOR OBTAINING A BLOOD SAMPLE

CROSS-REFERENCE TO RELATED APPLICATIONS

The present application is the United States national phase of International Application No. PCT/US2017/048143 filed Aug. 23, 2017, and claims priority to U.S. Provisional Application No. 62/378,971, filed Aug. 24, 2016, entitled "Finger-Based Capillary Blood Collection Device", the entire disclosures of which are hereby incorporated by reference.

BACKGROUND OF THE INVENTION

1. Field of the Disclosure

The present disclosure relates generally to a device for obtaining a biological sample. More particularly, the present disclosure relates to an integrated finger-based capillary blood collection device with the ability to lance and squeeze a finger, collect, stabilize, and dispense a blood sample in a controlled manner.

2. Description of the Related Art

Devices for obtaining and collecting biological samples, such as blood samples, are commonly used in the medical industry. One type of blood collection that is commonly done in the medial field is capillary blood collection which is often done to collect blood samples for testing. Certain diseases, such as diabetes, require that the patient's blood be tested on a regular basis to monitor, for example, the patient's blood sugar levels. Additionally, test kits, such as cholesterol test kits, often require a blood sample for analysis. The blood collection procedure usually involves pricking a finger or other suitable body part in order to obtain the blood sample. Typically, the amount of blood needed for such tests is relatively small and a small puncture wound or incision normally provides a sufficient amount of blood for these tests. Various types of lancet devices have been developed which are used for puncturing the skin of a patient to obtain a capillary blood sample from the patient.

Many different types of lancet devices are commercially available to hospitals, clinics, doctors' offices, and the like, as well as to individual consumers. Such devices typically include a sharp-pointed member such as a needle, or a sharp-edged member such as a blade, that is used to make a quick puncture wound or incision in the patient's skin in order to provide a small outflow of blood. It is often physiologically and psychologically difficult for many people to prick their own finger with a hand-held needle or blade. As a result, lancet devices have evolved into automatic devices that puncture or cut the skin of the patient upon the actuation of a triggering mechanism. In some devices, the needle or blade is kept in a standby position until it is triggered by the user, who may be a medical professional in charge of drawing blood from the patient, or the patient himself or herself. Upon triggering, the needle or blade punctures or cuts the skin of the patient, for example, on the finger. Often, a spring is incorporated into the device to provide the "automatic" force necessary to puncture or cut the skin of the patient.

One type of contact activated lancet device that features automatic ejection and retraction of the puncturing or cutting element from and into the device is U.S. Pat. No. 9,380,975, which is owned by Becton, Dickinson and Company, the assignee of the present application. This lancet device includes a housing and a lancet structure having a puncturing element. The lancet structure is disposed within the housing and adapted for movement between a retaining or pre-actuated position wherein the puncturing element is retained within the housing, and a puncturing position wherein the puncturing element extends through a forward end of the housing. The lancet device includes a drive spring disposed within the housing for biasing the lancet structure toward the puncturing position, and a retaining hub retaining the lancet structure in the retracted position against the bias of the drive spring. The retaining hub includes a pivotal lever in interference engagement with the lancet structure. An actuator within the housing pivots the lever, thereby moving the lancet structure toward the rearward end of the housing to at least partially compress the drive spring, and releasing the lever from interference engagement with the lancet structure. The blood sample that is received is then collected and/or tested. This testing can be done by a Point-of-Care (POC) testing device or it can be collected and sent to a testing facility.

Currently, capillary blood collection workflow is a complex multi-step process requiring high skill level. The multi-step nature of this process introduces several variables that could cause sample quality issues such as hemolysis, inadequate sample stabilization, and micro-clots. The use of lancet devices for obtaining blood samples can result in several variables that effect the collection of the capillary blood sample, including, but not limited to, holding the lancet still during the testing, obtaining sufficient blood flow from the puncture site, adequately collecting the blood, preventing clotting, and the like. Some of the most common sources of process variability are: (1) inadequate lancing site cleaning and first drop removal which can potentially result in a contaminated sample; (2) inconsistent lancing location and depth which could potentially result in insufficient sample volume and a large fraction of interstitial fluid; (3) inconsistent squeezing technique and excessive pressure near the lancing site to promote blood extraction (e.g., blood milking) which could potentially result in a hemolyzed sample; (4) variable transfer interfaces and collection technique which could potentially result in a hemolyzed or contaminated sample; and (5) inadequate sample mixing with anticoagulant which could potentially result in micro-clots.

Thus, there is a need in the art for a device that has the ability to lance and squeeze the finger, collect the sample, stabilize the sample, and subsequently dispense the sample in a controlled manner. There is also a need in the art for a device that simplifies and streamlines the capillary blood collection by eliminating workflow variabilities which are typically associated with low sample quality including hemolysis and micro-clots. There is still a further need in the art for a closed system collection and transfer that eliminate blood exposure and device reuse. There is still a further need in the art for a device that: (1) introduces flexibility in the accommodation of different capillary blood collection and transfer container; (2) has the capability to generate high quality uniformly mixed/stabilized capillary blood samples; (3) has the capability to generate on-board plasma from capillary plasma samples; (4) has the capability to collect large capillary blood samples (>50-5004) at reduced pain; (5) contains a unique sample identifier that is paired with patient information at the time of collection; (6) has the capability to collect capillary blood and perform on-board diagnostics; and (7) has multiple collection ports to collect a blood sample into different containers having the same or different anticoagulants.

SUMMARY OF THE INVENTION

The present disclosure is directed to a device for obtaining a biological sample, such as a capillary blood collection device, which meets the needs set forth above and has the ability to lance and squeeze the finger, collect the sample, stabilize the sample, and subsequently dispense the sample in a controlled manner. The device also simplifies and streamlines the capillary blood collection by eliminating workflow variabilities which are typically associated with low sample quality including hemolysis and micro-clots.

The present disclosure includes a self-contained and fully integrated finger-based capillary blood collection device with ability to lance, collect and stabilize high volume capillary blood sample, e.g., up to or above 500 microliters. The device simplifies and streamlines high volume capillary blood collection by eliminating workflow steps and variabilities which are typically associated with low sample quality including hemolysis, micro-clots, and patient discomfort. The device comprises a retractable lancing mechanism that can lance the finger and an associated blood flow path which ensures attachment and transfer of the capillary blood from the pricked finger site to the collection container. The device also includes a holder that can be cyclically squeezed to stimulate, i.e., pump, blood flow out of the finger and also anticoagulant deposited in the flow path or collection container to stabilize collected sample.

According to one design, the device can comprise discrete components such as a holder, a lancet, and a collection container. According to another design, the lancet and collection container can be integrated into one device which is then used with the holder. According to yet another design, the holder, lancet, and collection container can be integrated into a single system. Any of these designs are envisioned to be used as a self-standing disposable device and/or in association with an external power source for pain reduction control. The capillary blood collection device can serve as a platform for various capillary blood collection containers ranging from small tubes to capillary dispensers, as well as on-board plasma separation modules. This capability extends the product flexibility to various applications including dispensing to a Point-of-Care (POC) cartridge or to a small collection tube transfer which can be used in a centrifuge or an analytical instrument.

In accordance with an embodiment of the present invention, a device for obtaining a blood sample includes a holder for receiving a sample source, the holder having an actuation portion and a port; a lancet housing secured within the port, the lancet housing having an inlet and an interior; a puncturing element moveable between a pre-actuated position wherein the puncturing element is retained within the interior and a puncturing position wherein at least a portion of the puncturing element extends through the inlet; and a container removably connectable to a portion of the lancet housing, the container defining a collection cavity.

In one configuration, the actuation portion is transitionable between a first position in which the holder defines a first diameter, such as a first elliptical shape, and a second position in which the holder defines a second diameter, such as a second elliptical shape, wherein the second diameter is less than the first diameter, and the first elliptical shape is different from the second elliptical shape. In another configuration, the actuation portion includes a contact member.

In yet another configuration, the actuation portion is transitionable between a first position in which the contact member is in a disengaged position and a second position in which the contact member is in an engaged position. In one configuration, with the contact member in the engaged position, the contact member exerts a pressure on the sample source. In another configuration, the actuation portion includes a pumping member for applying pressure to the sample source. In yet another configuration, the pumping member comprises a pair of opposed tabs. In one configuration, the sample source is a finger. In another configuration, with the finger received within the holder, the port is in communication with a portion of the finger. In yet another configuration, the puncturing element comprises a hollow needle. In one configuration, with the container connected to the lancet housing, the longitudinal axis of the port, the lancet housing, and the container are aligned. In another configuration, the lancet housing includes an outlet. In yet another configuration, with the container connected to the lancet housing, the outlet of the lancet housing is in fluid communication with the collection cavity of the container. In one configuration, with the finger received within the holder and the puncturing element in the puncturing position, the puncturing element lances the finger to draw the blood sample. In another configuration, the blood sample flows through the hollow needle to the outlet to the collection cavity. In yet another configuration, with the container connected to the lancet housing, the longitudinal axis of the lancet housing is at an angle to the longitudinal axis of the container. In one configuration, the device includes a capillary tube. In another configuration, with the container connected to the lancet housing, the capillary tube is in fluid communication with the inlet of the lancet housing and the collection cavity of the container. In yet another configuration, with the finger received within the holder and the puncturing element in the puncturing position, the puncturing element lances the finger to draw the blood sample. In one configuration, the blood sample flows through the capillary tube to the collection cavity.

In accordance with another embodiment of the present invention, a device for obtaining a blood sample includes a holder for receiving a sample source, the holder having an actuation portion and a port, wherein the actuation portion is transitionable between a first position in which the holder defines a first diameter, such as a first elliptical shape, and a second position in which the holder defines a second diameter, such as a second elliptical shape, wherein the second diameter is less than the first diameter, and the first elliptical shape is different than the second elliptical shape.

In one configuration, the actuation portion includes a contact member. In another configuration, the actuation portion is transitionable between the first position in which the contact member is in a disengaged position and the second position in which the contact member is in an engaged position. In yet another configuration, with the contact member in the engaged position, the contact member exerts a pressure on the sample source. In one configuration, the actuation portion includes a pumping member for applying pressure to the sample source. In another configuration, the pumping member comprises a pair of opposed tabs. In yet another configuration, the sample source is a finger. In one configuration, with the finger received within the holder, the port is in communication with a portion of the finger. In another configuration, the holder includes a stability extension portion. In yet another configuration, the device includes a lancet housing removably connectable to the port, the lancet housing having an inlet and an interior; and a puncturing element moveable between a pre-actuated position wherein the puncturing element is retained within the interior and a puncturing position wherein at least a portion of the puncturing element extends through the inlet. In one configuration, the device includes a container removably connectable to the port, the container defining a collection cavity. In another configuration, the device includes a lancet housing removably connectable to the port, the lancet housing having an inlet and an interior; a puncturing element moveable between a pre-actuated position wherein the puncturing element is retained within the interior and a puncturing position wherein at least a portion of the puncturing element extends through the inlet; and a container removably connectable to a portion of the lancet housing, the container defining a collection cavity.

BRIEF DESCRIPTION OF THE DRAWINGS

The above-mentioned and other features and advantages of this disclosure, and the manner of attaining them, will become more apparent and the disclosure itself will be better understood by reference to the following descriptions of embodiments of the disclosure taken in conjunction with the accompanying drawings, wherein:

FIG. 25 is a perspective view of a third step of using an integrated device of the present disclosure in accordance with an embodiment of the present invention.

FIG. 26 is a perspective view of a fourth step of using an integrated device of the present disclosure in accordance with an embodiment of the present invention.

Corresponding reference characters indicate corresponding parts throughout the several views. The exemplifications set out herein illustrate exemplary embodiments of the disclosure, and such exemplifications are not to be construed as limiting the scope of the disclosure in any manner.

DETAILED DESCRIPTION

Figure 1:
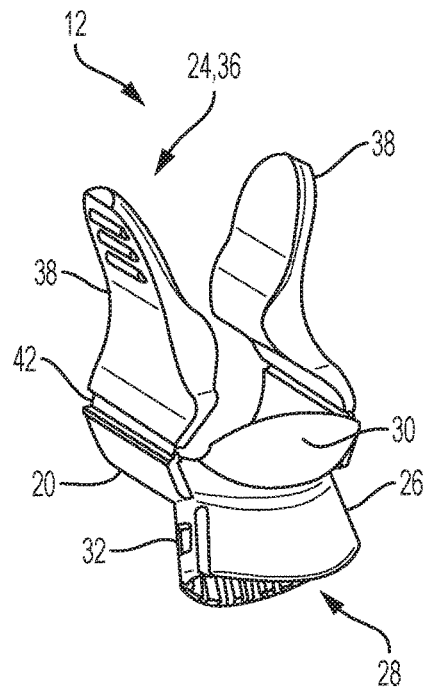
FIG. 1 is a perspective view of a holder in accordance with an embodiment of the present invention.

The following description is provided to enable those skilled in the art to make and use the described embodiments contemplated for carrying out the invention. Various modifications, equivalents, variations, and alternatives, however, will remain readily apparent to those skilled in the art. Any and all such modifications, variations, equivalents, and alternatives are intended to fall within the spirit and scope of the present invention.

For purposes of the description hereinafter, the terms "upper", "lower", "right", "left", "vertical", "horizontal", "top", "bottom", "lateral", "longitudinal", and derivatives thereof shall relate to the invention as it is oriented in the drawing figures. However, it is to be understood that the invention may assume alternative variations and step sequences, except where expressly specified to the contrary. It is also to be understood that the specific devices and processes illustrated in the attached drawings, and described in the following specification, are simply exemplary embodiments of the invention. Hence, specific dimensions and other physical characteristics related to the embodiments disclosed herein are not to be considered as limiting.

The present disclosure is directed to a device for obtaining a biological sample, such as a capillary blood collection device, which meets the needs set forth above and has the ability to lance and squeeze the finger, collect the sample, stabilize the sample, and subsequently dispense the sample in a controlled manner. The device also simplifies and streamlines the capillary blood collection by eliminating workflow variabilities which are typically associated with low sample quality including hemolysis and micro-clots.

The present disclosure includes a self-contained and fully integrated finger-based capillary blood collection device with ability to lance, collect and stabilize high volume capillary blood sample, e.g., up to or above 500 microliters. The device simplifies and streamlines high volume capillary blood collection by eliminating workflow steps and variabilities which are typically associated with low sample quality including hemolysis, micro-clots, and patient discomfort. The device comprises a retractable lancing mechanism that can lance the finger and an associated blood flow path which ensures attachment and transfer of the capillary blood from the pricked finger site to the collection container. The device also includes a holder that can be cyclically squeezed to stimulate, i.e., pump, blood flow out of the finger and also anticoagulant deposited in the flow path or collection container to stabilize collected sample.

According to one design, the device can comprise discrete components such as a holder, a lancet, and a collection container. According to another design, the lancet and collection container can be integrated into one device which is then used with the holder. According to yet another design, the holder, lancet, and collection container can be integrated into a single system. Any of these designs are envisioned to be used as a self-standing disposable device and/or in association with an external power source for pain reduction control. The capillary blood collection device can serve as a platform for various capillary blood collection containers ranging from small tubes to capillary dispensers, as well as on-board plasma separation modules. This capability extends the product flexibility to various applications including dispensing to a Point-of-Care (POC) cartridge or to a small collection tube transfer which can be used in a centrifuge or an analytical instrument.

Figure 7A:
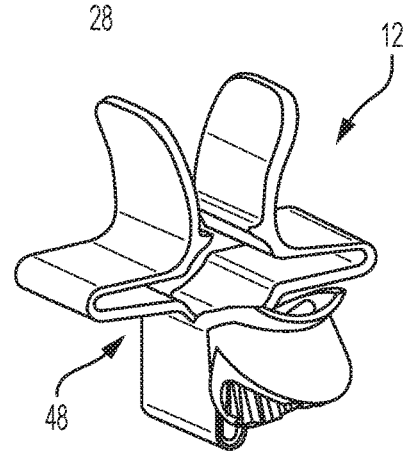
FIG. 7A is a perspective view of a holder in accordance with another embodiment of the present invention.
Figure 7B:
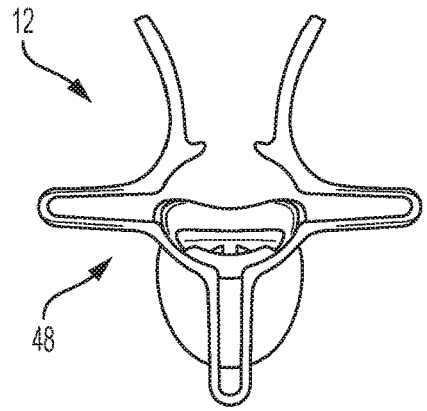
FIG. 7B is a perspective view of a holder in accordance with another embodiment of the present invention.
Figure 8:
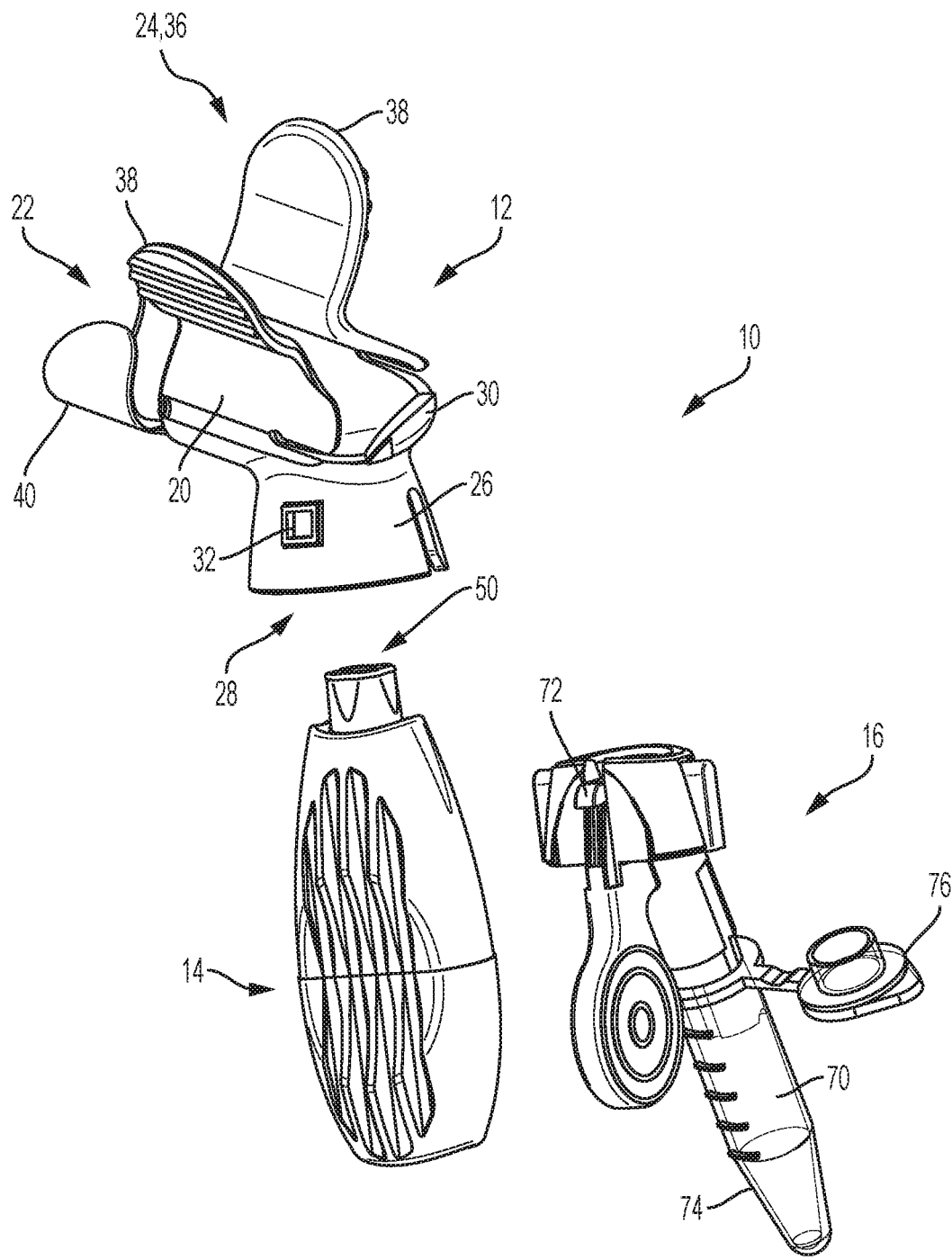
FIG. 8 is an exploded, perspective view of a device having discrete components for obtaining a blood sample in accordance with an embodiment of the present invention.
Figure 9:
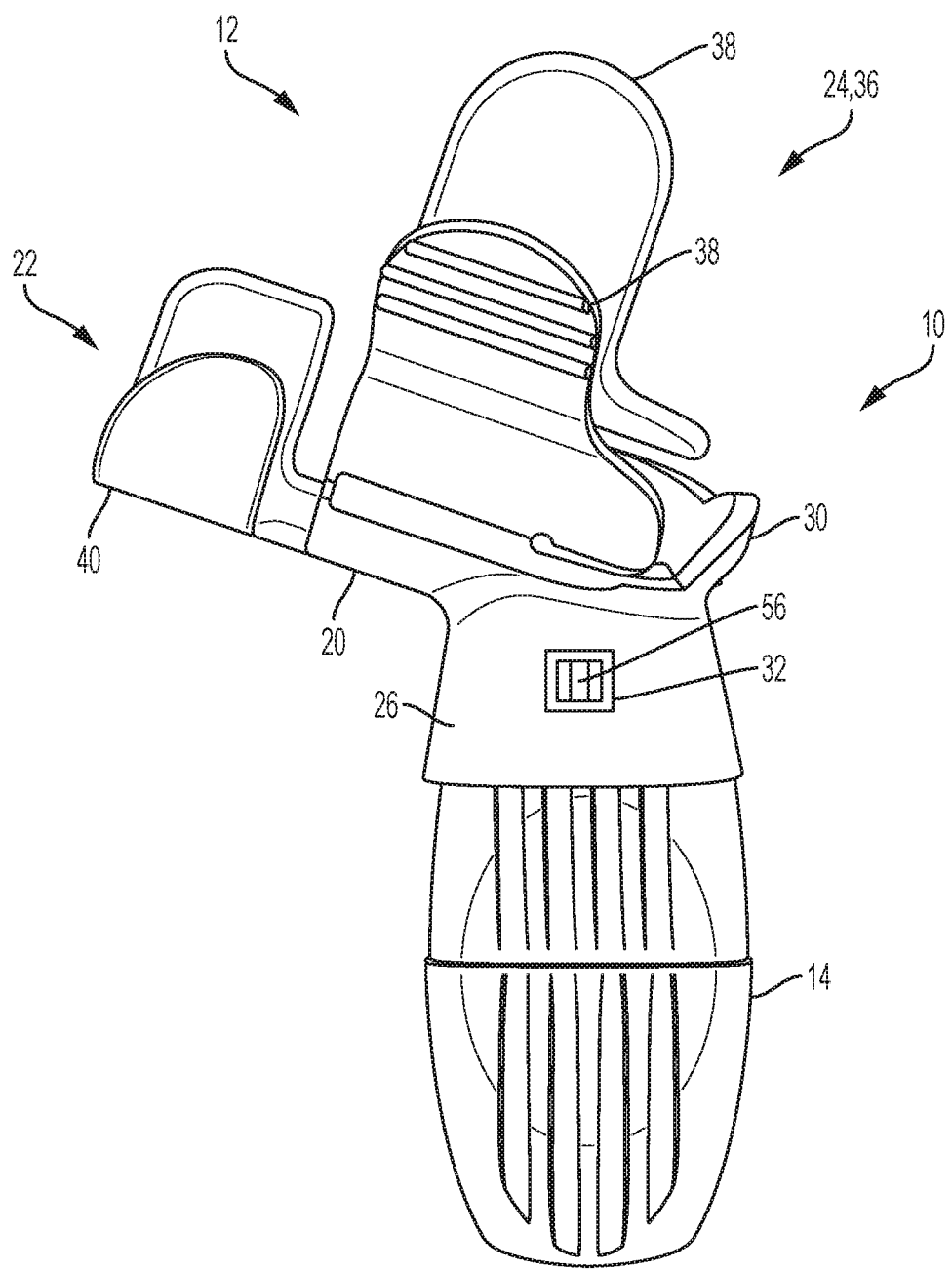
FIG. 9 is a perspective view of a holder with a lancet housing secured within a port in accordance with an embodiment of the present invention.
Figure 10:
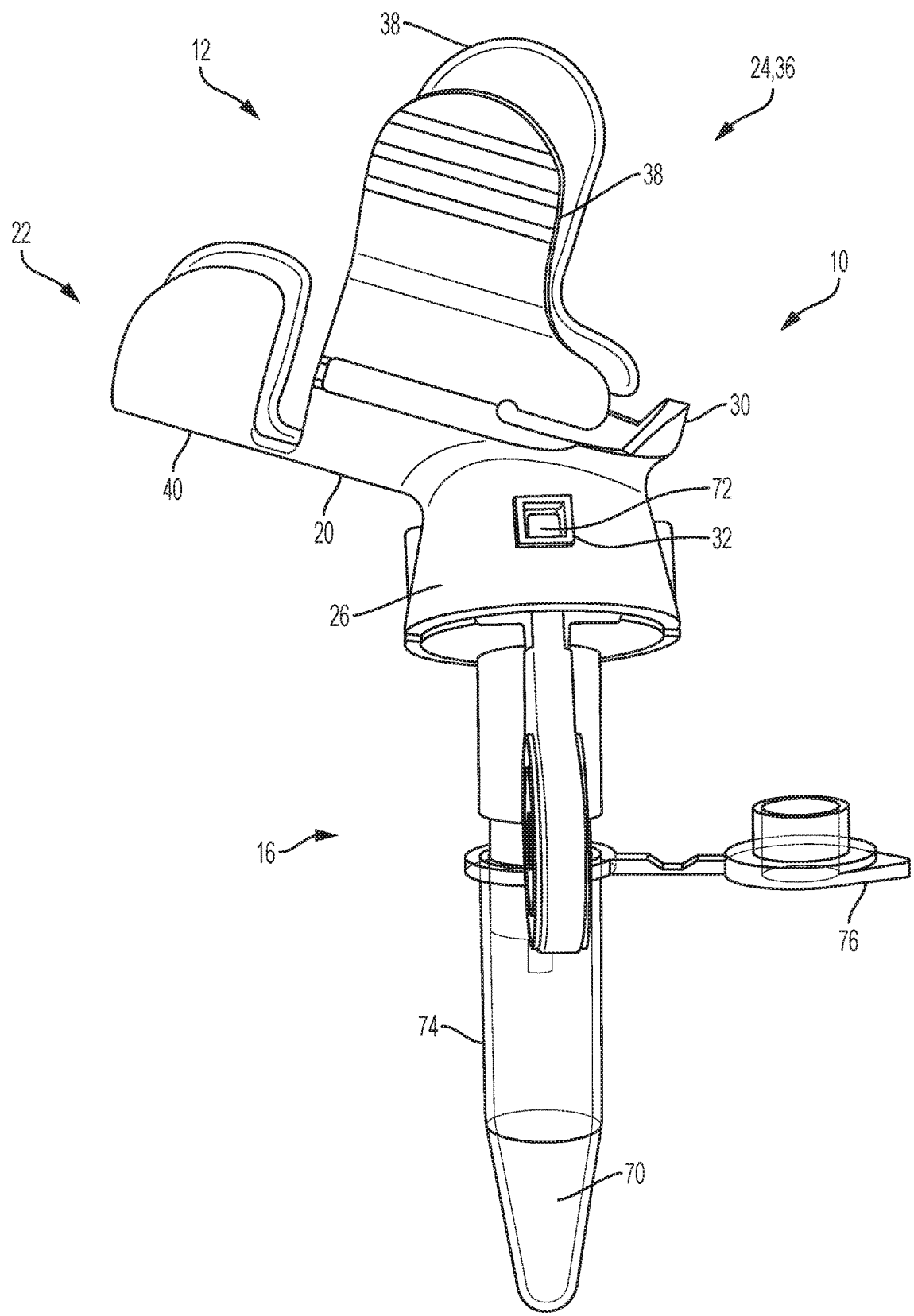
FIG. 10 is a perspective view of a holder with a container secured within a port in accordance with an embodiment of the present invention.

Referring to FIGS. 8-10, in an exemplary embodiment, a device 10 of the present disclosure includes discrete components, e.g., a holder 12 (as shown in FIGS. 1-7B), a lancet housing or lancet 14, and a collection container 16.

Figure 11:
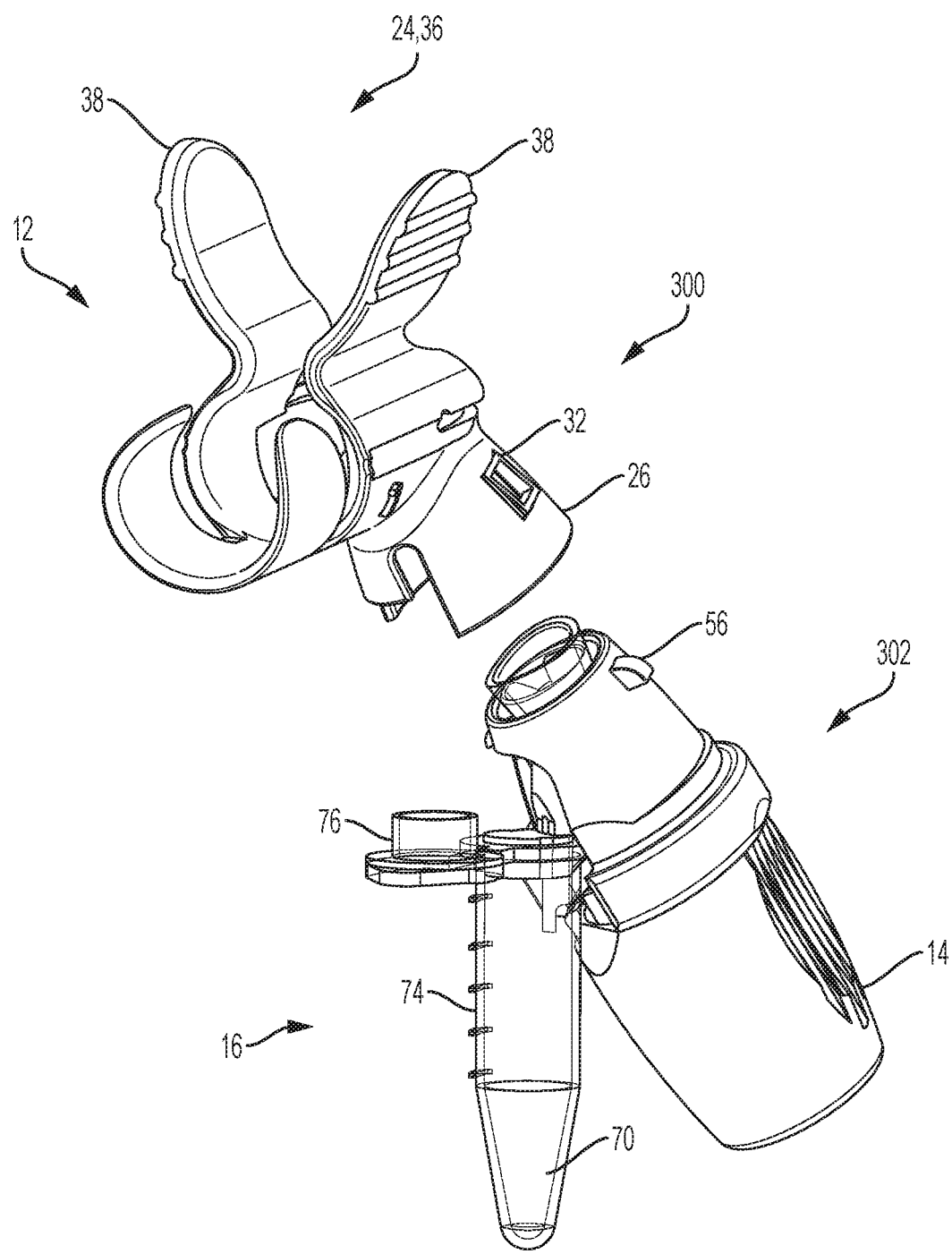
FIG. 11 is a perspective view of a semi-integrated device for obtaining a blood sample with an at-angle flow in accordance with another embodiment of the present invention.
Figure 12:
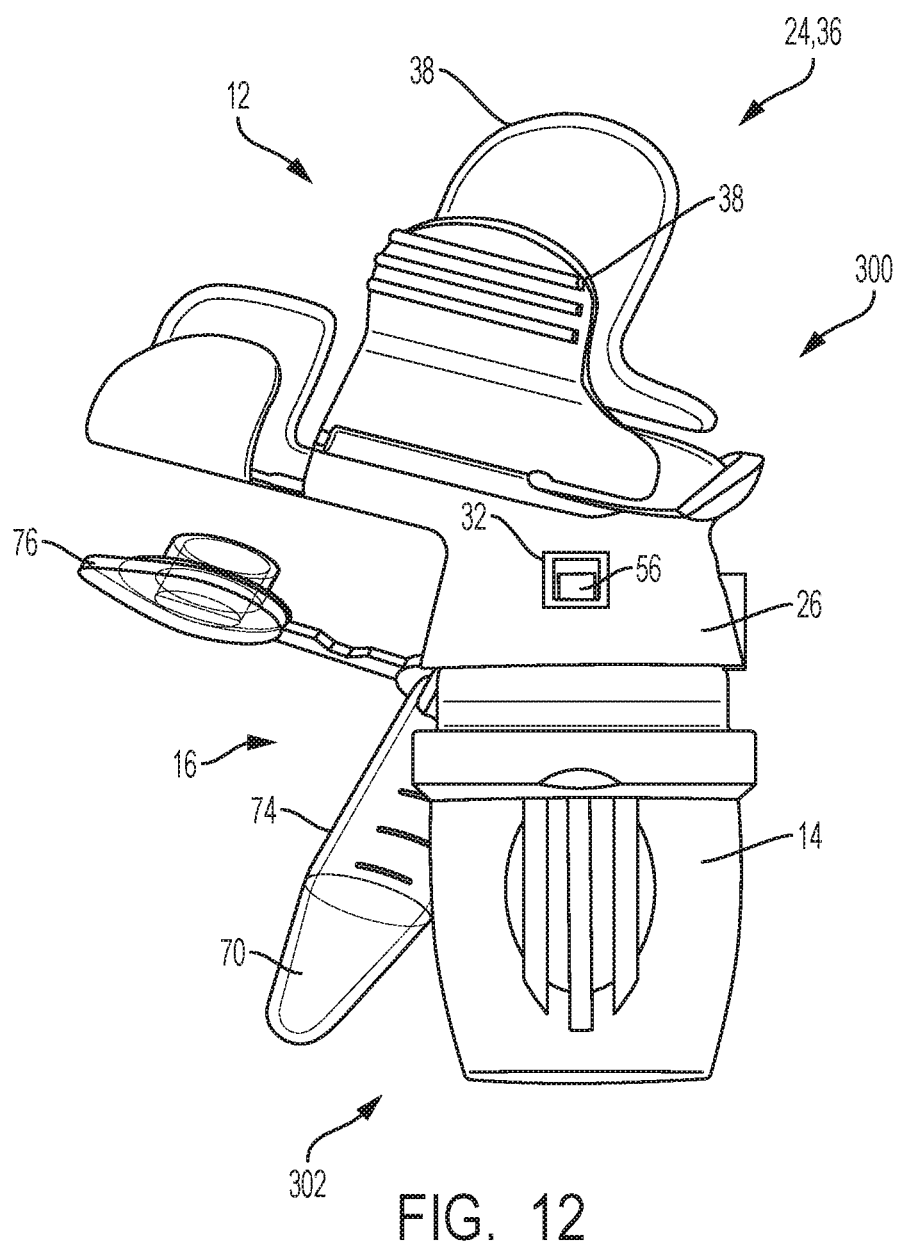
FIG. 12 is a perspective view of a holder with a lancet housing and container secured within a port in accordance with another embodiment of the present invention.
Figure 13:
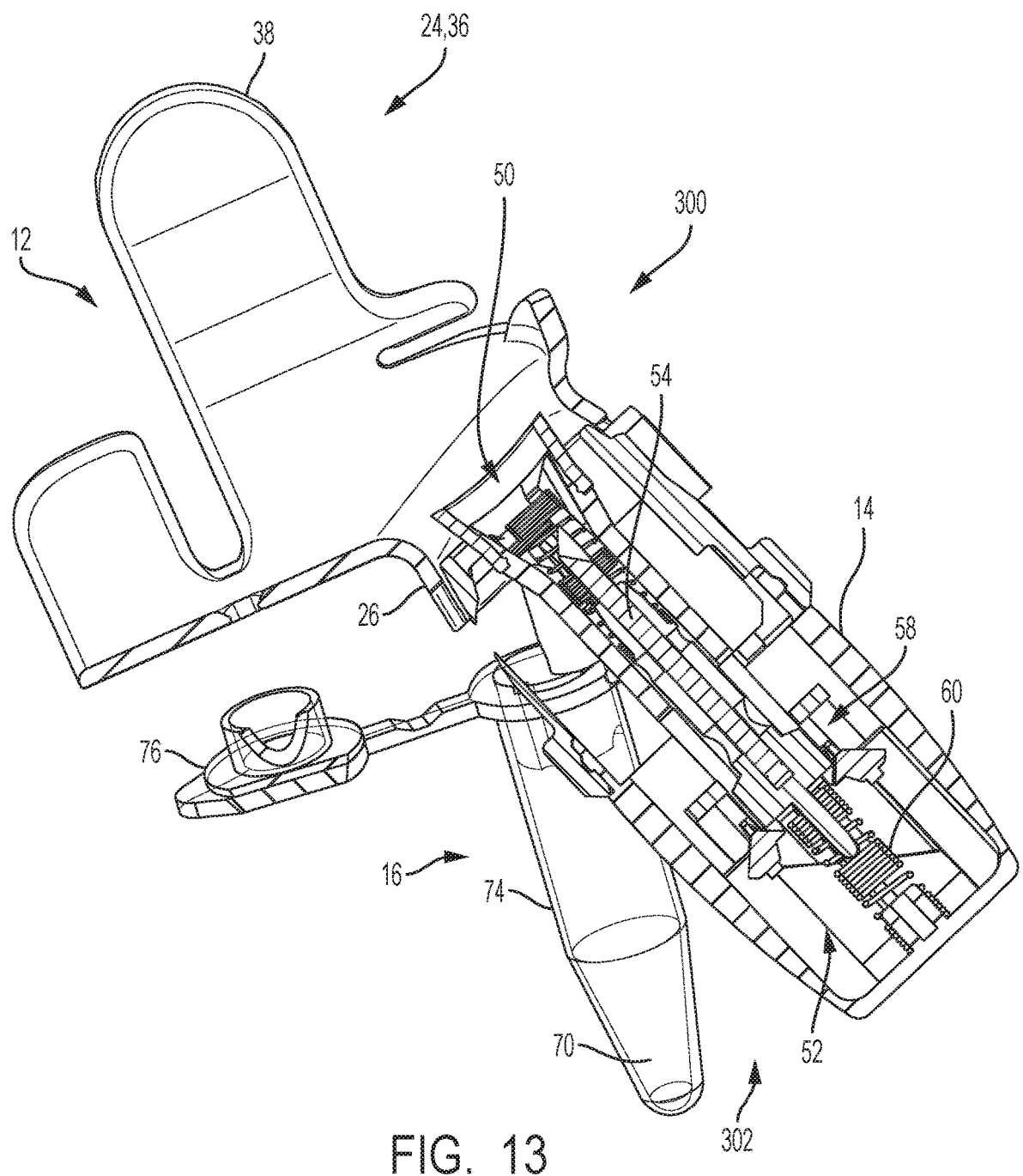
FIG. 13 is a cross-sectional view of the device of FIG. 12 in accordance with another embodiment of the present invention.
Figure 14:
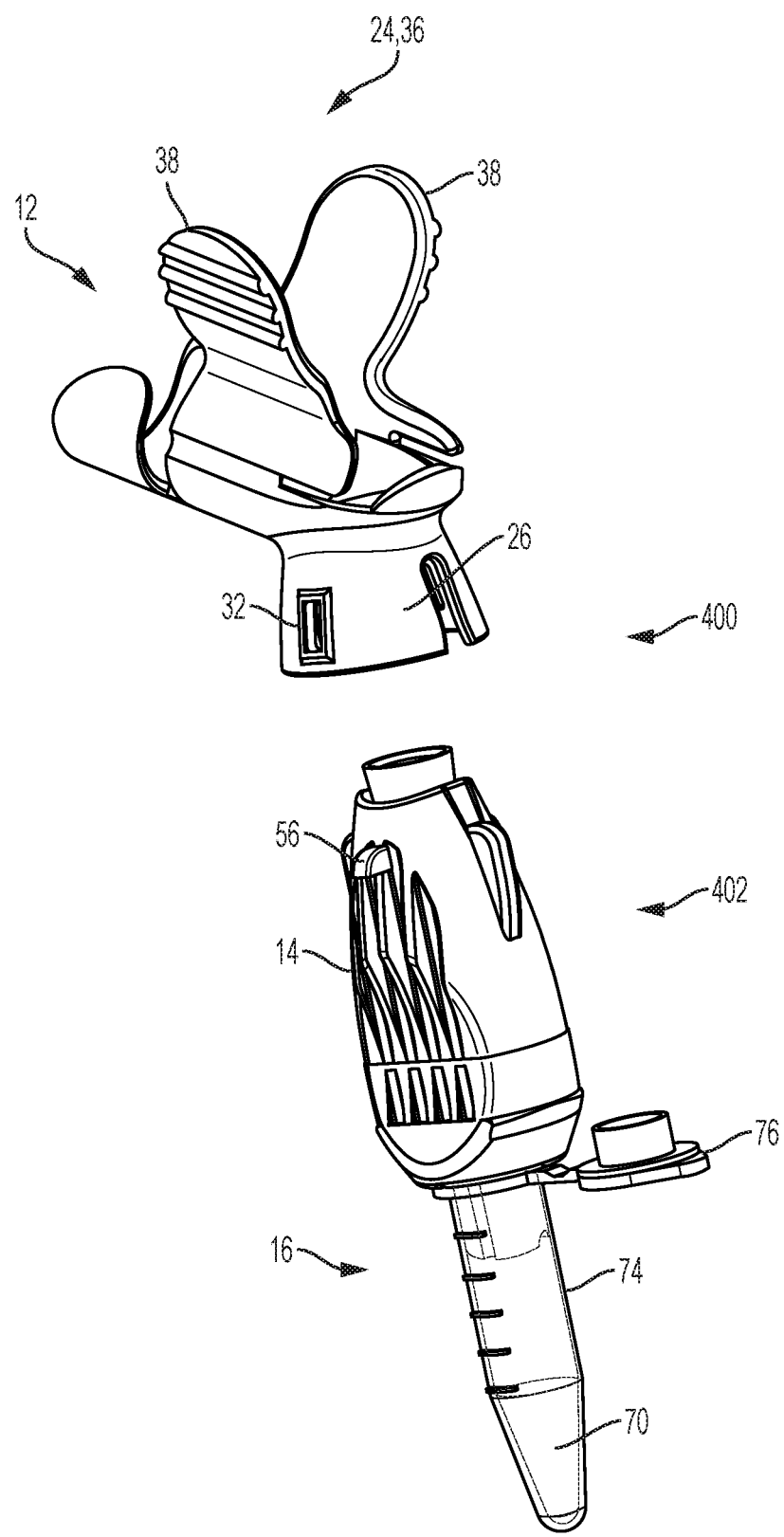
FIG. 14 is a perspective view of a semi-integrated device for obtaining a blood sample with an in-line flow in accordance with another embodiment of the present invention.
Figure 15:
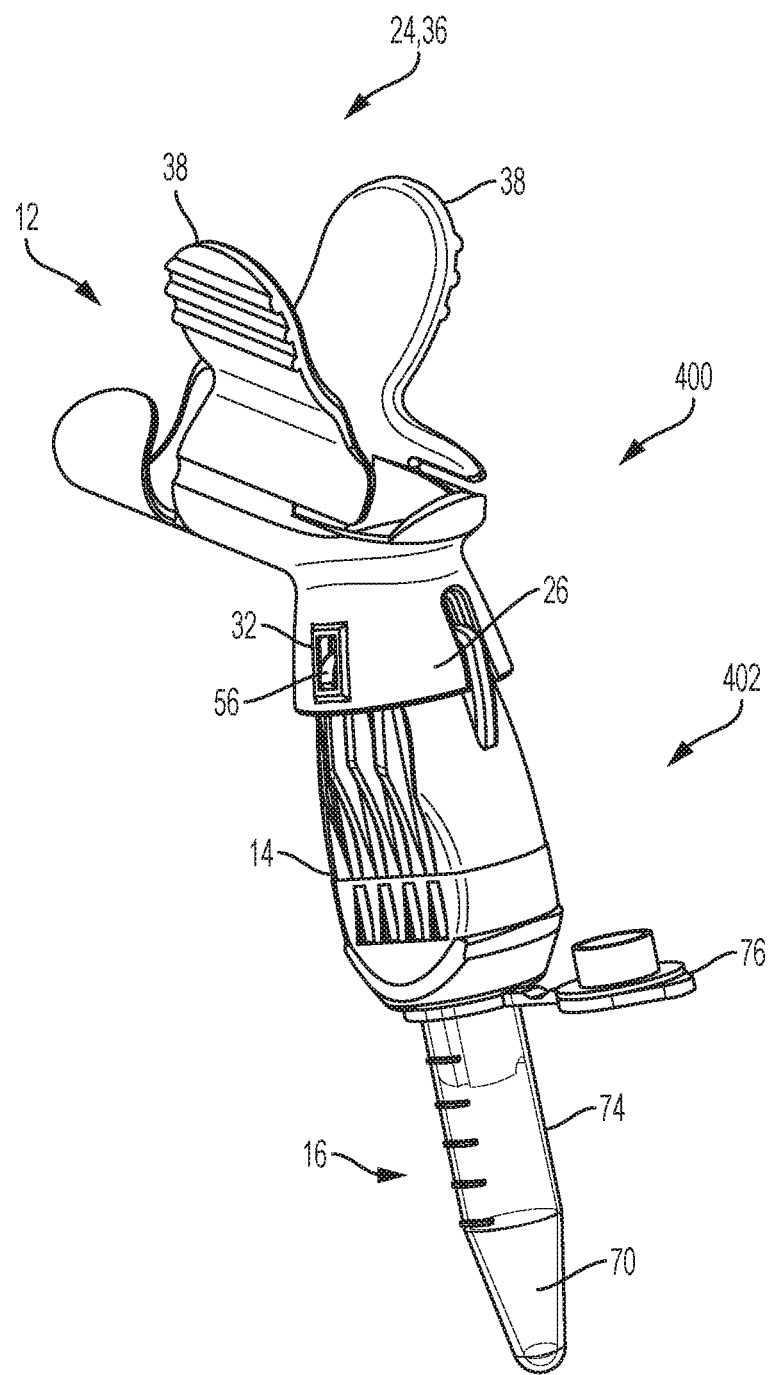
FIG. 15 is a perspective view of a holder with a lancet housing and container secured within a port in accordance with another embodiment of the present invention.
Figure 16:
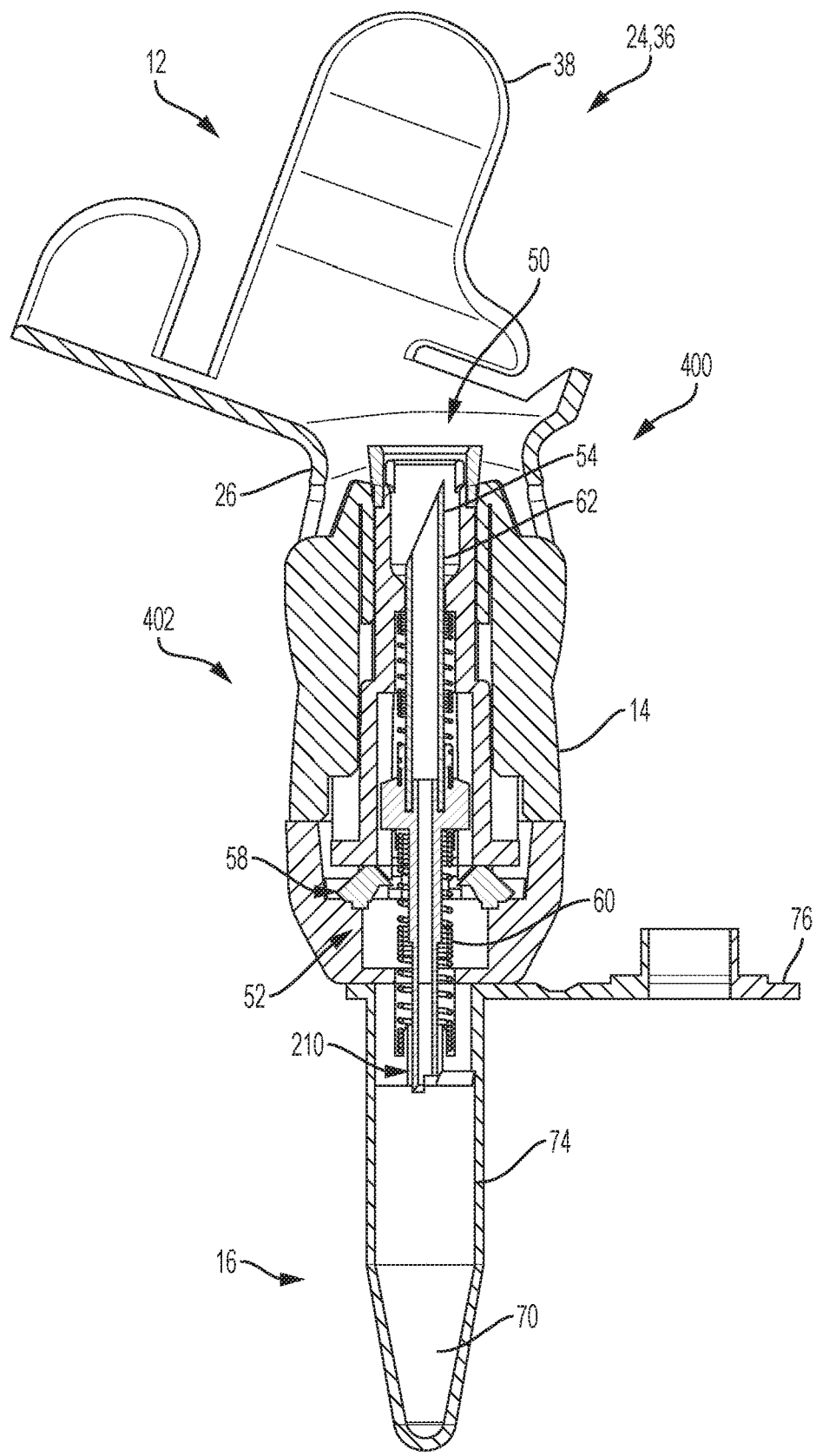
FIG. 16 is a cross-sectional view of the device of FIG. 15 in accordance with another embodiment of the present invention.

Referring to FIGS. 11-13, in another exemplary embodiment, a semi-integrated device 300 of the present disclosure has an at-angle flow and includes an integrated lancet housing and collection container which can be connected with a separate holder. Referring to FIGS. 14-16, in another exemplary embodiment, a semi-integrated device 400 of the present disclosure has an in-line flow and includes an integrated lancet housing and collection container which can be connected with a separate holder.

Figure 17:
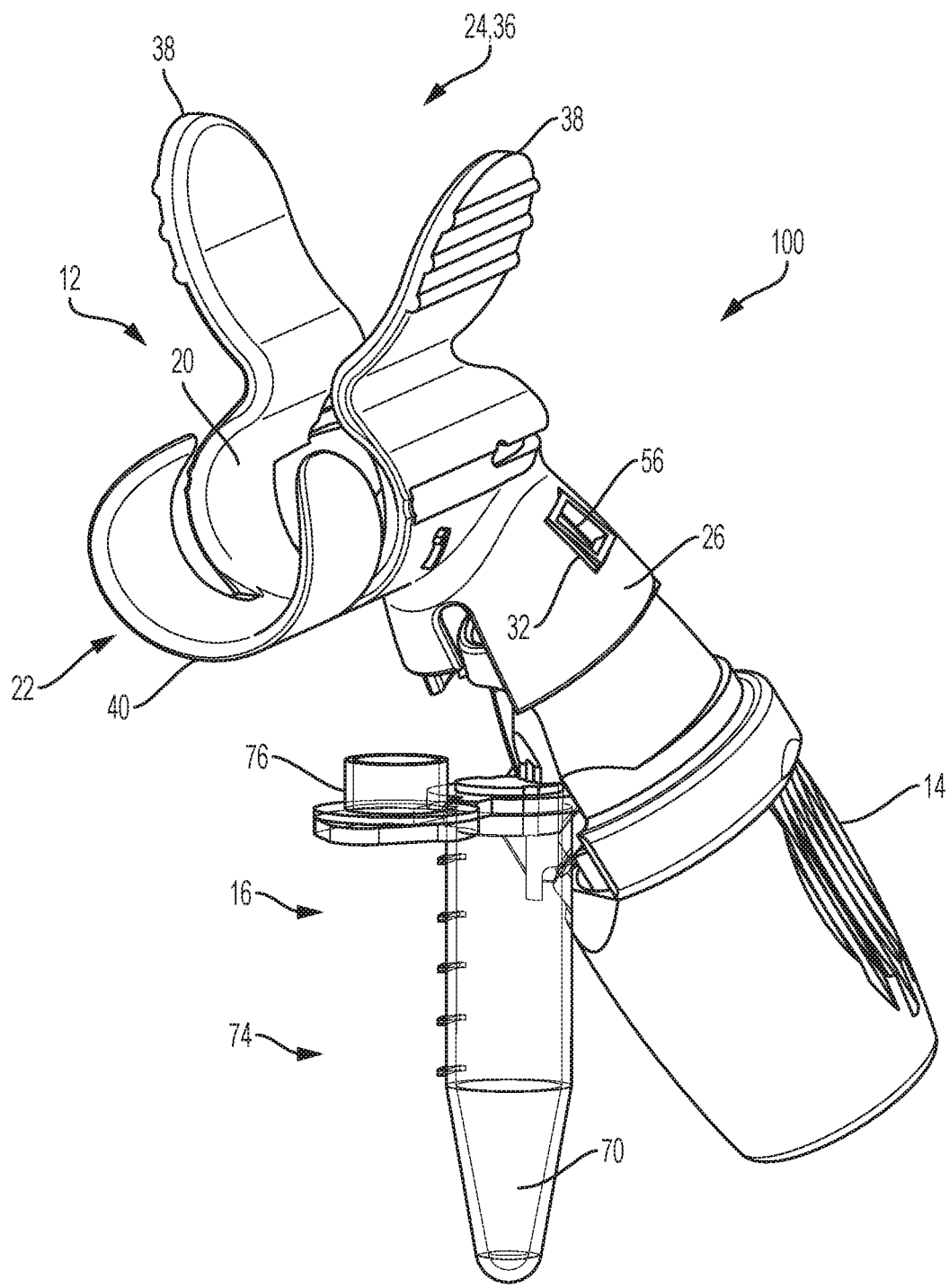
FIG. 17 is a perspective view of an integrated device for obtaining a blood sample with an at-angle flow in accordance with another embodiment of the present invention.
Figure 18:
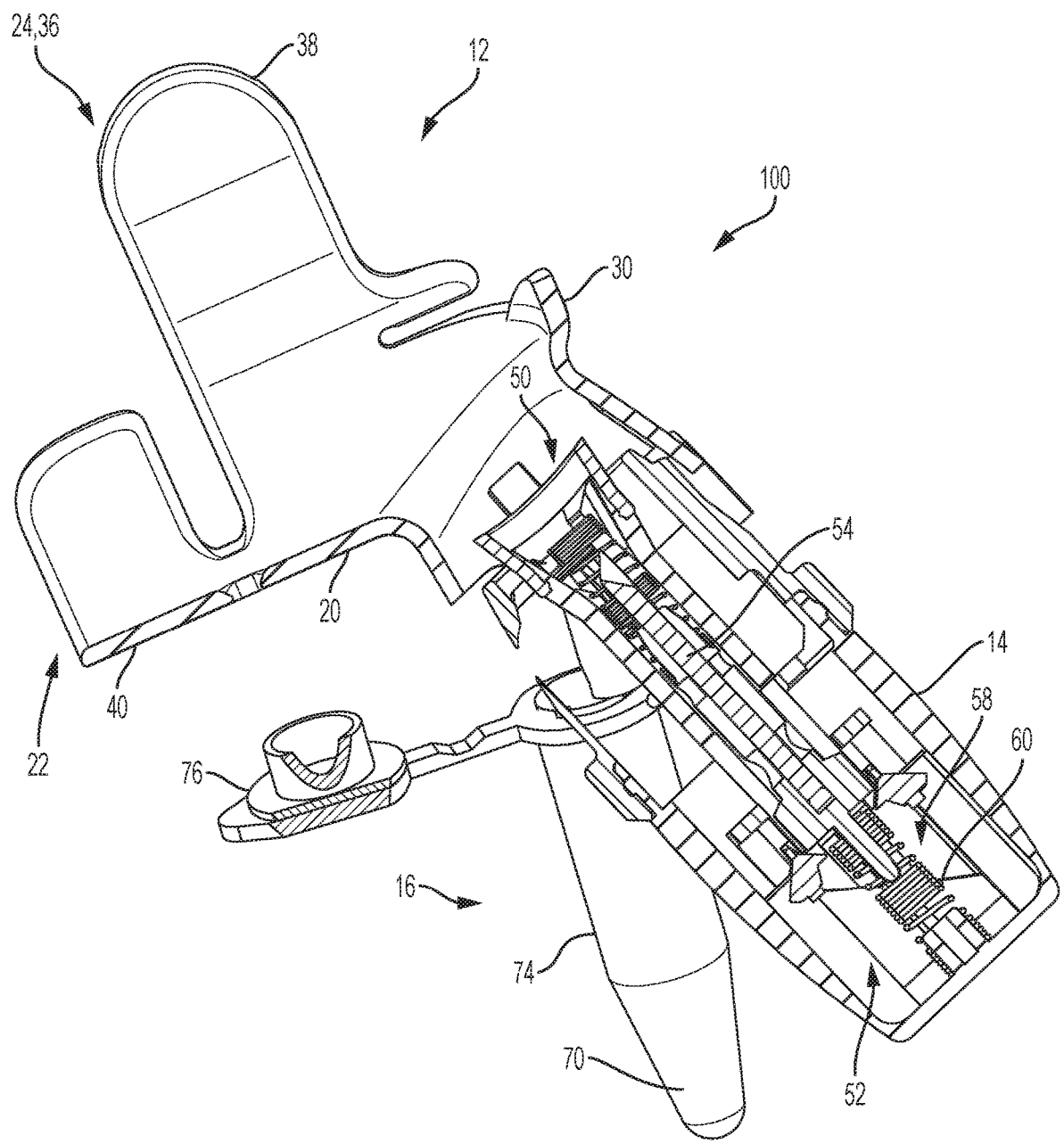
FIG. 18 is a cross-sectional view of the device of FIG. 17 in accordance with another embodiment of the present invention.
Figure 19:
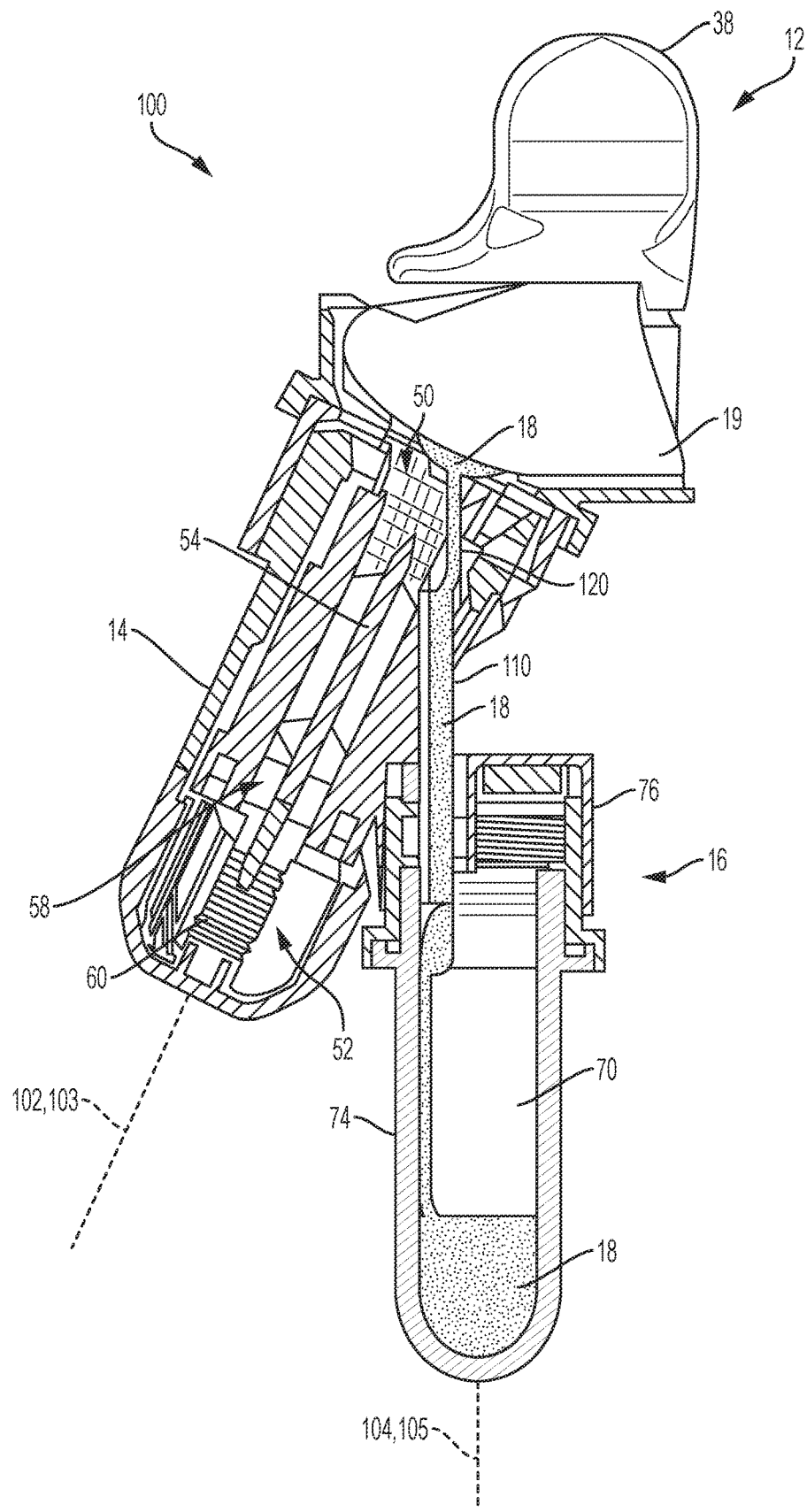
FIG. 19 is a cross-sectional view of the device of FIG. 17 showing a blood flow path in accordance with another embodiment of the present invention.
Figure 20:
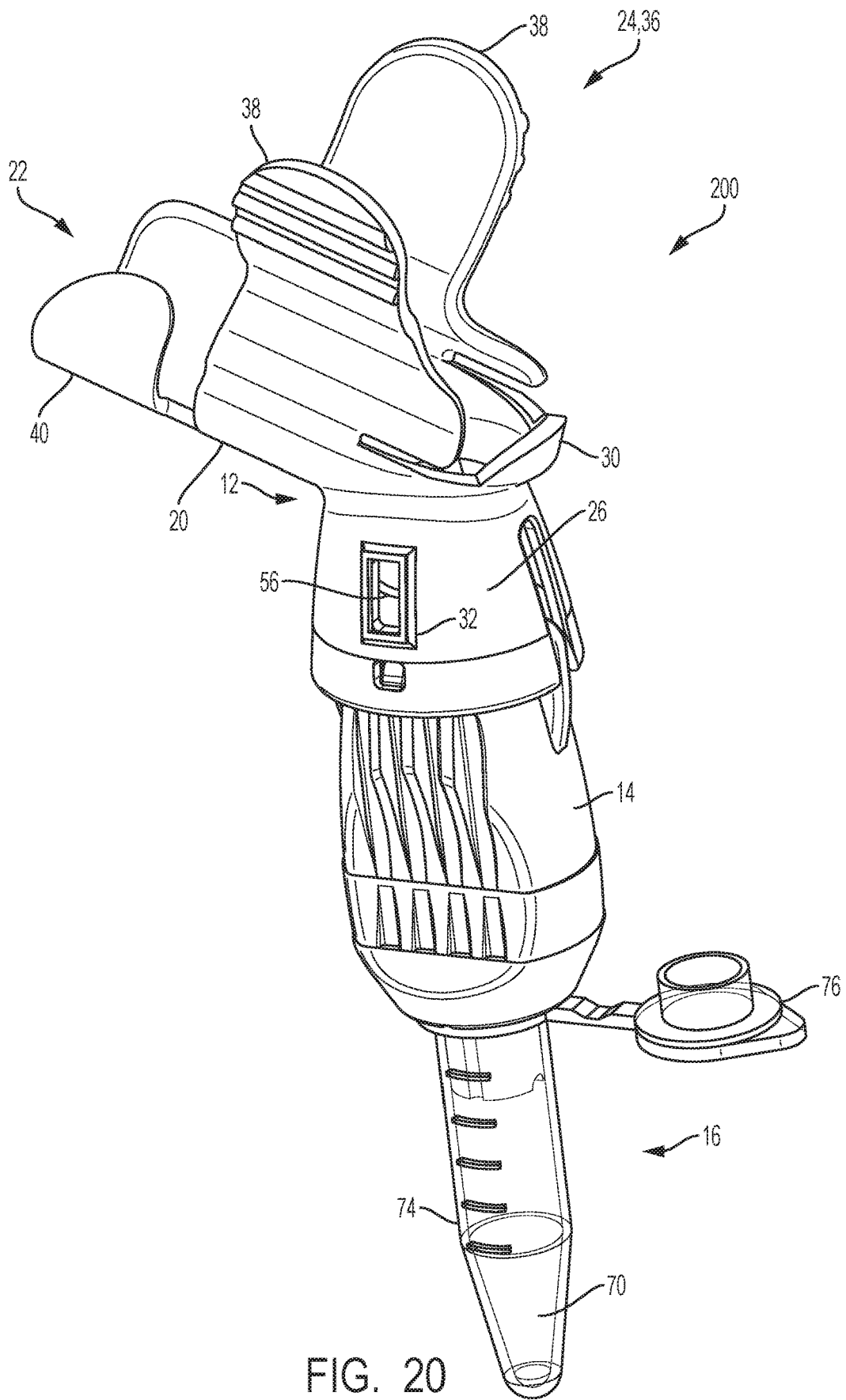
FIG. 20 is a perspective view of an integrated device for obtaining a blood sample with an in-line flow in accordance with another embodiment of the present invention.
Figure 21:
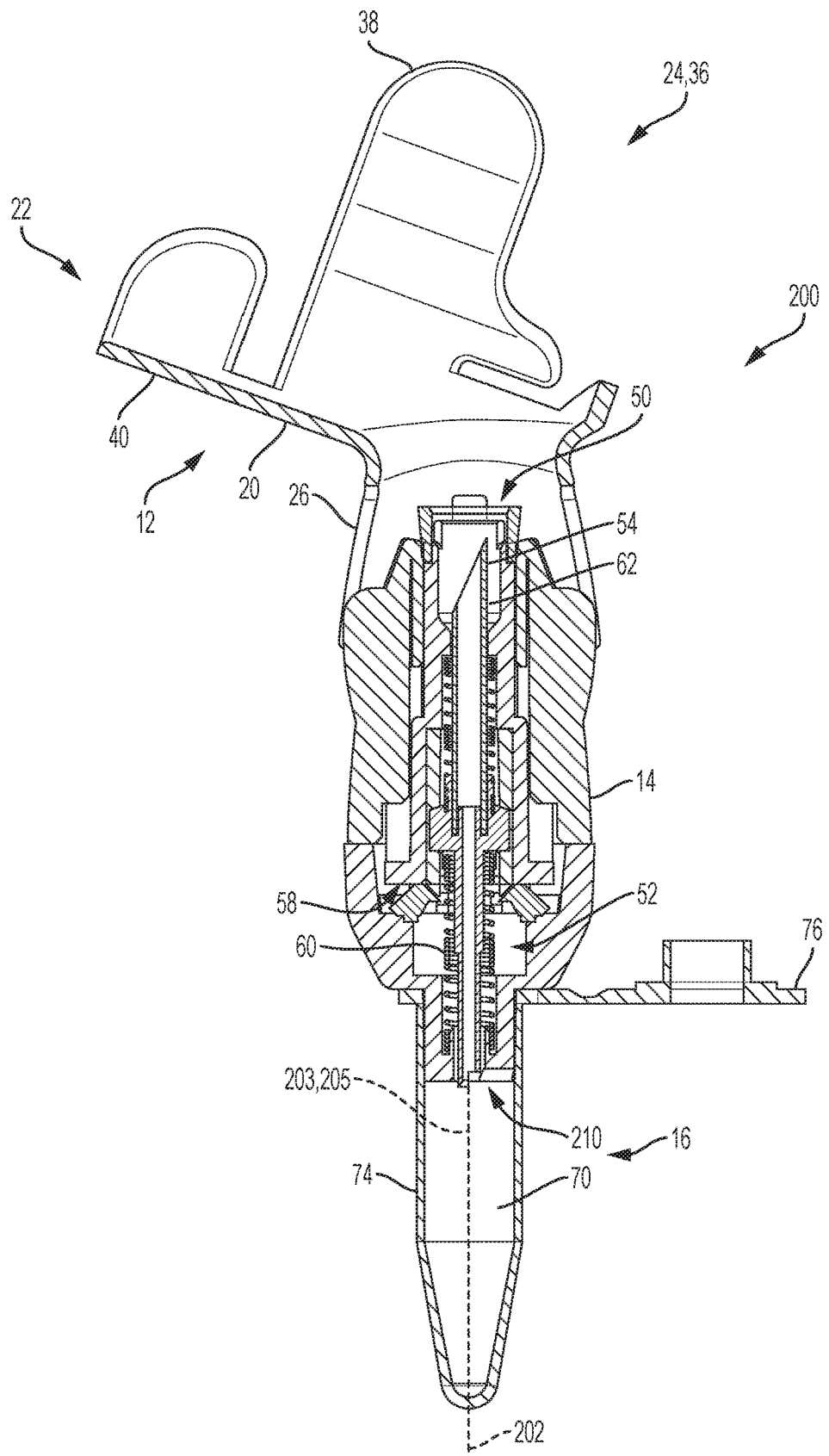
FIG. 21 is a cross-sectional view of the device of FIG. 20 in accordance with another embodiment of the present invention.
Figure 22:
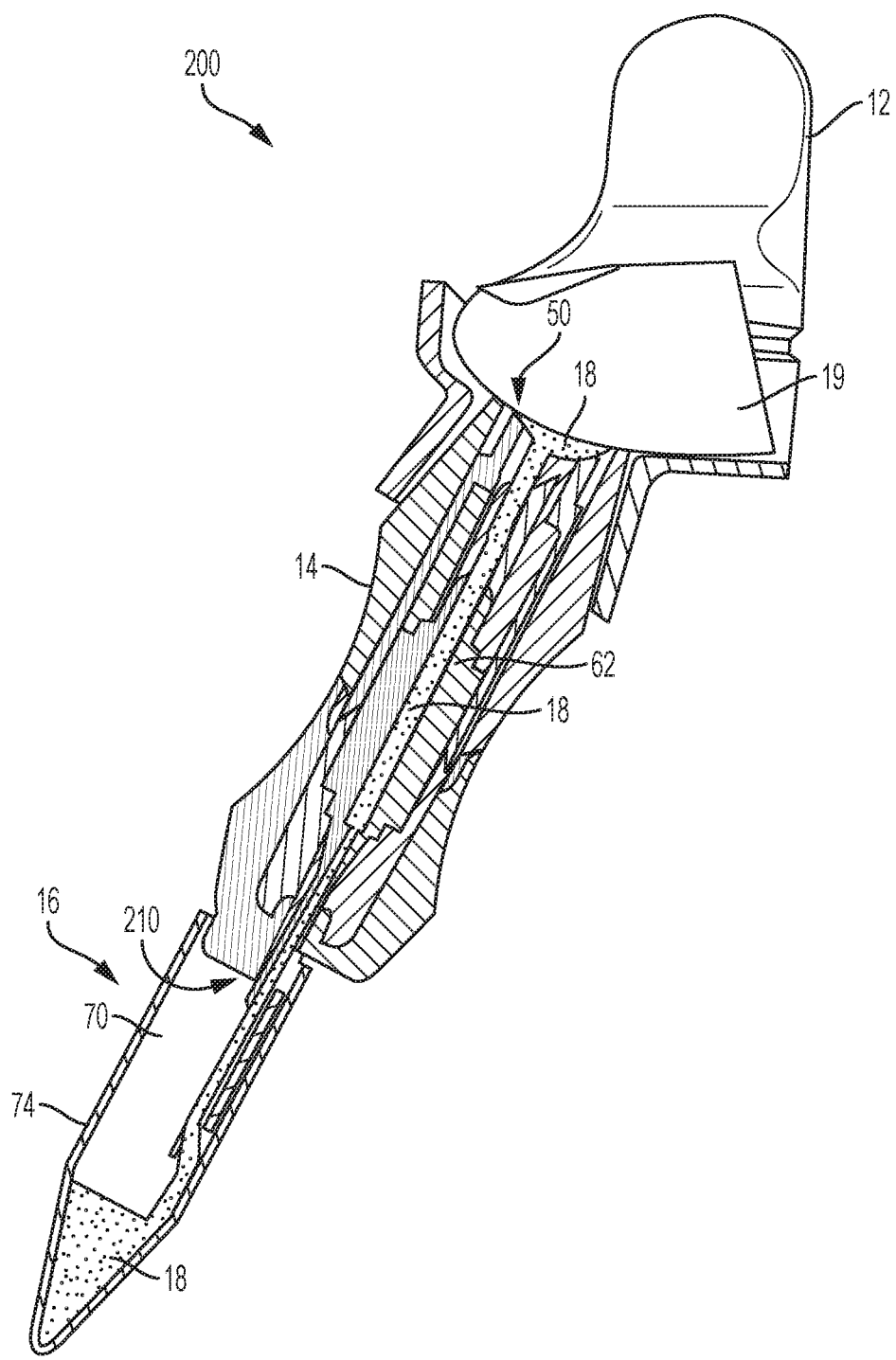
FIG. 22 is a cross-sectional view of the device of FIG. 20 showing a blood flow path in accordance with another embodiment of the present invention.

Referring to FIGS. 17-19, in another exemplary embodiment, an integrated device 100 of the present disclosure has an at-angle flow and includes an integrated holder, lancet housing, and collection container. Referring to FIGS. 20-22, in another exemplary embodiment, an integrated device 200 of the present disclosure has an in-line flow and includes an integrated holder, lancet housing, and collection container.

Referring to FIGS. 8-10, in an exemplary embodiment, a device 10 for obtaining a blood sample 18 includes separate components, e.g., a holder 12, a lancet housing or lancet 14, and a collection container 16. FIGS. 1-7B illustrate exemplary embodiments of a holder or finger housing 12 of the present disclosure.

Referring to FIGS. 1-7B, exemplary embodiments of holders 12 of the present disclosure that are able to receive a sample source, e.g., a finger 19, for supplying a biological sample, such as a blood sample 18. A holder 12 of the present disclosure generally includes a finger receiving portion 20 having a first opening 22 (FIG. 5), an actuation portion 24, a port 26 having a second opening 28, and a finger end guard 30. In one embodiment, the finger end guard 30 provides a stop portion for properly aligning and securing a finger 19 within the holder 12.

The first opening 22 of the finger receiving portion 20 is configured for receiving a sample source, e.g., a finger 19, for supplying a biological sample, such as a blood sample 18. It can be appreciated that the sample source could include other parts of the body capable of fitting within the first opening 22. The port 26 is in communication with the finger receiving portion 20. For example, with a finger 19 received within the holder 12, the port 26 is in communication with a portion of the finger 19. A holder 12 of the present disclosure can be sized to accommodate all finger sizes.

The second opening 28 of the port 26 is configured for receiving a lancet housing 14 and a collection container 16 as described in more detail below. In one embodiment, the port 26 includes a locking portion 32 for securely receiving the lancet housing 14 and the collection container 16 within the port 26.

In one embodiment, the actuation portion 24 is transitionable between a first position (FIG. 2) in which the holder 12 defines a first diameter and a second position (FIG. 3) in which the holder 12 defines a second diameter, wherein the second diameter is less than the first diameter. In one embodiment, the actuation portion 24 is transitionable between a first position (FIG. 2) in which the holder 12 defines a first elliptical shape, and a second position (FIG. 3) in which the holder 12 defines a second elliptical shape, wherein the first elliptical shape is different than the second elliptical shape. In this manner, with the holder 12 in the second position with a reduced diameter, a portion of the holder 12 contacts the sample source and the actuation portion 24 of the holder 12 is able to pump and/or extract blood 18 as described in more detail below.

Figure 2:
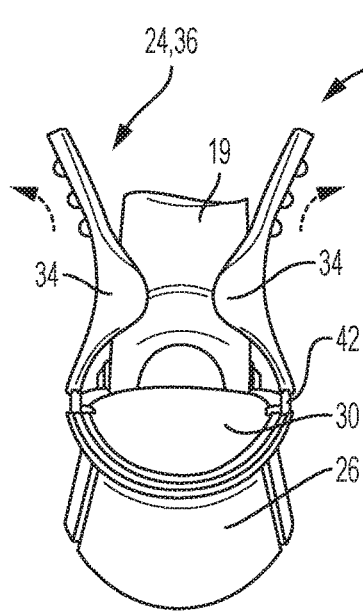
FIG. 2 is a perspective view of a holder in a first position in accordance with an embodiment of the present invention.
Figure 3:
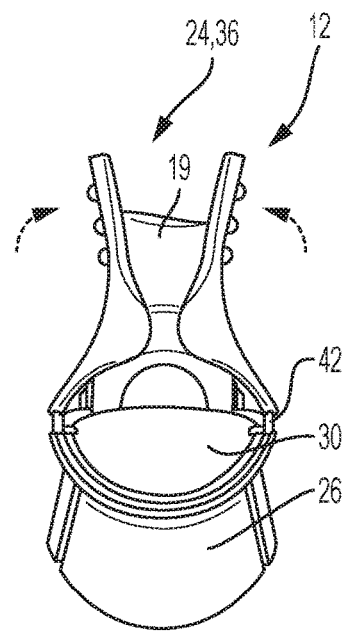
FIG. 3 is a perspective view of a holder in a second position in accordance with an embodiment of the present invention.

Referring to FIGS. 2 and 3, in one embodiment, the actuation portion 24 includes a contact member 34. Referring to FIG. 2, with the actuation portion 24 in the first position, the contact member 34 is in a disengaged position, i.e., the contact member 34 is provided in a first position with respect to a sample source, e.g., the finger 19, such that the contact member 34 may be in slight contact therewith. Referring to FIG. 3, with the actuation portion 24 in the second position, the contact member 34 is in an engaged position, i.e., the contact member 34 is provided in a second position with respect to the sample source, e.g., the finger 19, such that the contact member 34 is in an applied pressure contact with the finer 19, and the actuation portion 24 of the holder 12 is able to pump and/or extract blood 18. For example, with the contact member 34 in the engaged position, the contact member 34 exerts a pressure on the sample source.

Referring to FIGS. 2 and 3, in one embodiment, the actuation portion 24 includes a pumping member 36 for applying pressure to the sample source, e.g., the finger 19. In one embodiment, the pumping member 36 comprises a pair of opposed tabs or wings 38. In such an embodiment, each tab 38 may include a contact member 34. Referring to FIGS. 1-3, in one embodiment, the holder 12 includes a living hinge portion 42. The living hinge portion 42 allows a user to squeeze the wings 38 between a first position (FIG. 2) and a second position (FIG. 3).

Advantageously, the holder 12 of the present disclosure allow a user to repeatedly squeeze and release the wings 38 to pump and/or extract blood 18 from a finger 19 until a desired amount of blood 18 is filled in a collection container 16.

Advantageously, with the holder 12 placed onto a finger 19, the holder 12 does not constrict the blood flow and defines lancing and finger squeezing locations. The squeezing tabs or wings 38 provide a pre-defined range of squeezing pressure that is consistently applied throughout a finger 19. By doing so, the holder 12 provides a gentle controlled finger massage that stimulates blood extraction and minimizes any potential hemolysis.

Figure 5:
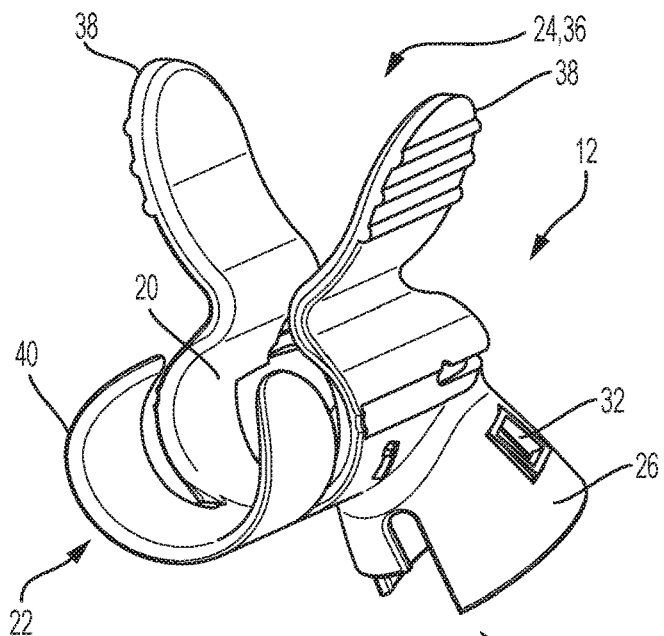
FIG. 5 is a perspective view of a holder in accordance with another embodiment of the present invention.
Figure 6A:
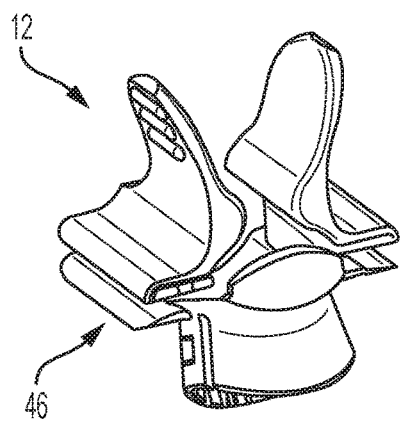
FIG. 6A is a perspective view of a holder in accordance with another embodiment of the present invention.
Figure 6B:
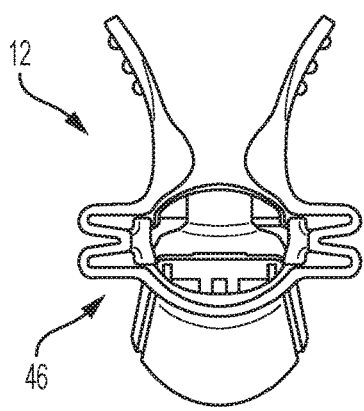
FIG. 6B is a perspective view of a holder in accordance with another embodiment of the present invention.

Referring to FIG. 5, in one embodiment, the holder 12 includes a stability extension portion 40. This provides additional support for the holder 12 to be securely placed onto a finger 19. In one embodiment, the finger receiving portion 20 forms a generally C-shaped member and includes a plurality of inner gripping members for providing additional grip and support for the holder 12 to be securely placed onto a finger 19.

In one embodiment, the finger receiving portion 20 is formed of a flexible material. In some embodiments, the finger receiving portion 20 and the port 26 are formed from a flexible material.

Figure 4A:
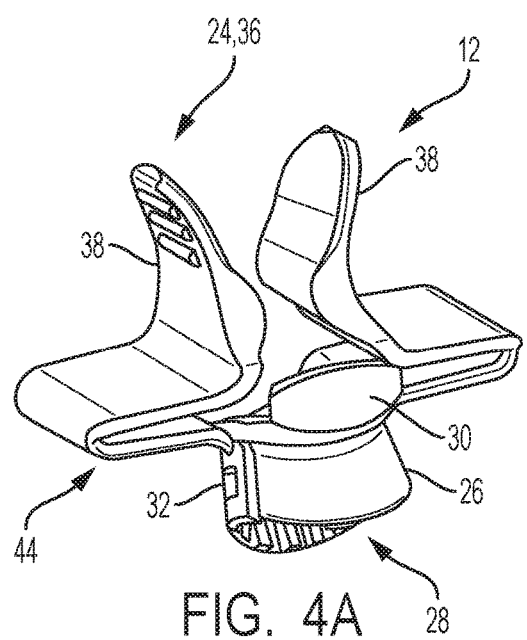
FIG. 4A is a perspective view of a holder in accordance with another embodiment of the present invention.
Figure 4B:
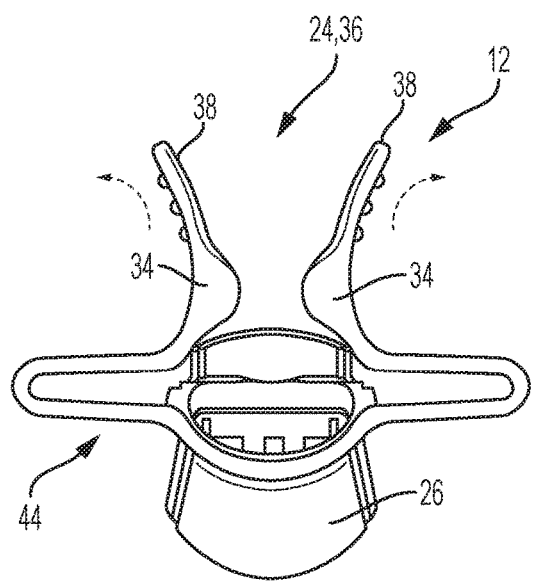
FIG. 4B is a perspective view of a holder in accordance with another embodiment of the present invention.

FIGS. 4A-7B illustrate other exemplary embodiments of the holder 12 of the present disclosure. Referring to FIGS. 4A-4B, the holder 12 includes a leaf spring 44. Referring to FIGS. 6A-6B, the holder 12 includes a double leaf spring 46. Referring to FIGS. 7A-7B, the holder 12 includes a triple leaf spring 48.

A device 10 for obtaining a blood sample 18 of the present disclosure includes a lancet housing or lancet 14 that is removably connectable to a port 26 of a holder 12. Referring to FIGS. 8, 9, and 13, in one embodiment, the lancet housing 14 includes an inlet or opening 50, an interior 52, a puncturing element 54, an engagement portion 56, a retractable mechanism 58, and a drive spring 60. In one embodiment, the puncturing element 54 is moveable between a pre-actuated position wherein the puncturing element 54 is retained within the interior 52 of the lancet housing 14 and a puncturing position wherein at least a portion of the puncturing element 54 extends through the inlet 50 of the lancet housing 14 to lance a portion of a finger 19.

In one embodiment, the lancet 14 of the present disclosure is a contact activated lancet and may be constructed in accordance with the features disclosed in U.S. Patent Application Publication No. 2006/0052809 filed May 6, 2005, entitled "Contact Activated Lancet Device", and commonly assigned with the present application, the entire disclosure of which is hereby expressly incorporated herein by reference thereto.

Referring to FIGS. 8-10, in one embodiment, the lancet housing 14 may be a separate component from the holder 12 and the collection container 16. Referring to FIGS. 11-16, in some embodiments, the collection container 16 and the lancet housing 14 form a single component that is removably connectable to the port 26 of the holder 12. Referring to FIGS. 17-22, in some embodiments, the collection container 16, the lancet housing 14, and the holder 12 form a single component.

Referring to FIGS. 8-10, in one embodiment, with the holder 12 and the lancet housing 14 being separate components, the lancet housing 14 is removably connectable to the port 26 of the holder 12. In such an embodiment, the lancet housing 14 includes an engagement portion 56. Referring to FIG. 9, in one embodiment, the lancet housing 14 is pushed into the port 26 of the holder 12 such that the engagement portion 56 of the lancet housing 14 is locked within the locking portion 32 of the holder 12. In this manner, the lancet housing 14 is securely connected and locked to the holder 12 such that the puncturing element 54 of the lancet housing 14 can be activated to lance or puncture a sample source, e.g., a finger 19. In some embodiments, the port 26 of the holder 12 includes a plurality of ribs for securing and locking the lancet 14 or the collection container 16 in the port 26.

To activate the lancet 14, the lancet 14 is pushed against a finger 19 to activate a retractable mechanism 58 of the lancet 14 to lance a finger 19. The lancet 14 of the present disclosure consistently delivers correct lancing depth and a pre-defined lancing location, thus ensuring a sufficient sample volume.

In one embodiment, the lancet 14 includes a drive spring 60 disposed within the interior 52 of the lancet housing 14 for biasing the puncturing element 54 toward the puncturing position. After puncturing, the puncturing element 54 is immediately retracted and safely secured within the interior 52 of the lancet housing 14.

Referring to FIGS. 8-10, in one embodiment, the lancet 14 of the present disclosure is used to lance the skin of a finger 19 and then a blood sample 18 is squeezed into a collection container 16 as described in more detail below.

Referring to FIG. 19, in one embodiment, the lancet housing 14 of the present disclosure is used to lance the skin of a finger 19 along a lance path and then a blood sample 18 flows down a blood flow path at an angle to the lance path as described in more detail below.

Referring to FIGS. 21 and 22, in one embodiment, the lancet 14 includes a hollow needle 62. In such an embodiment, the lancet housing 14 of the present disclosure is used to lance the skin of a finger 19 along a lance path and then a blood sample 18 flows along a parallel blood flow path through the hollow needle 62 as described in more detail below.

A device 10 for obtaining a blood sample 18 of the present disclosure includes a collection container 16 that is removably connectable to the port 26 of the holder 12. The collection container 16 defines a collection cavity 70 for receiving a blood sample 18, a container engagement portion 72, a blood collector portion 74, and a cap or septum 76. Once a desired amount of blood 18 is collected within the container 16, a blood collector portion 74 is detached from the collection device 10 in order to send a collected sample 18 to a diagnostic instrument and/or testing device. The blood collector portion 74 is sealed via the cap or septum 76 once removed from the collection device 10 to protectively seal the blood sample 18 within the collection cavity 70.

Referring to FIGS. 8-10, in one embodiment, the collection container 16 may be a separate component from the holder 12 and the lancet housing 14. Referring to FIGS. 11-16, in some embodiments, the collection container 16 and the lancet housing 14 form a single component that is removably connectable to the port 26 of the holder 12. Referring to FIGS. 17-22, in some embodiments, the collection container 16, the lancet housing 14, and the holder 12 form a single component.

Referring to FIGS. 8-10, in one embodiment, with the holder 12 and the collection container 16 being separate components, the container 16 is removably connectable to the port 26 of the holder 12. In such an embodiment, the container 16 includes a container engagement portion 72. Referring to FIG. 10, in one embodiment, the container 16 is pushed into the port 26 of the holder 12 such that the container engagement portion 72 of the container 16 is locked within the locking portion 32 of the holder 12. In this manner, the container 16 is securely connected and locked to the holder 12 such that a blood sample 18 can safely flow from the finger 19 within the holder 12 to the collection cavity 70 of the container 16.

It can be appreciated that several types of collection containers 16 can be used with the device 10 of the present disclosure. It can also be appreciated that the collection container 16 can be associated with a separate dispensing unit or the collection container 16 can include an integral dispensing portion for dispensing the blood 18 to a testing device.

Referring to FIGS. 8-10 and 27-31, use of a device 10 of the present disclosure having discrete components, e.g., a holder 12, a lancet housing or lancet 14, and a collection container 16, will now be described.

Figure 27:
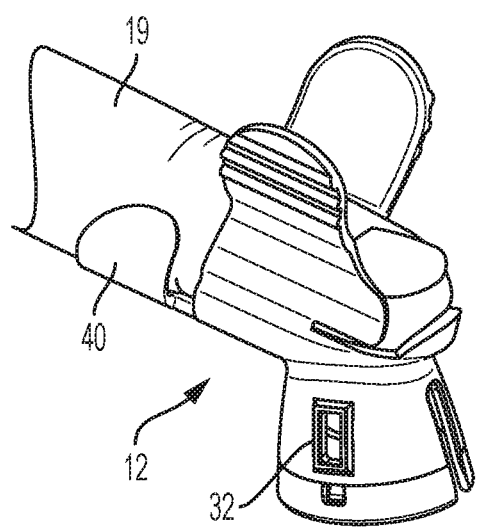
FIG. 27 is a perspective view of a first step of using a device having discrete components of the present disclosure in accordance with another embodiment of the present invention.

Referring to FIG. 27, first a desired finger 19 is cleaned and a holder 12 having an appropriate size for the desired finger 19 is selected and placed onto the finger 19 securely. Next, referring to FIG. 28, a lancet housing 14 is connected to the port 26 of the holder 12. As discussed above, the lancet housing 14 is pushed into the port 26 of the holder 12 such that the engagement portion 56 of the lancet housing 14 is locked within the locking portion 32 of the holder 12. In this manner, the lancet housing 14 is securely connected and locked to the holder 12 such that the puncturing element 54 (FIG. 13) of the lancet housing 14 can be activated to lance or puncture a sample source, e.g., a finger 19. With the lancet 14 connected to the port 26 of the holder 12, the lancet is in communication with the finger 19.

Figure 28:
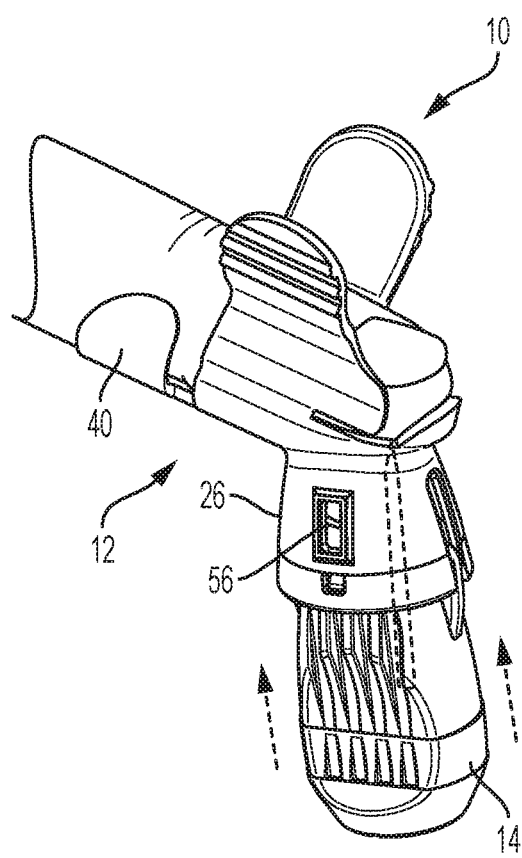
FIG. 28 is a perspective view of a second step of using a device having discrete components of the present disclosure in accordance with another embodiment of the present invention.

Referring to FIG. 28, when it is desired to activate the lancet 14 to lance the skin of a finger 19, the lancet 14 is pushed against a finger 19 to activate a retractable mechanism 58 (FIG. 13) of the lancet 14 to lance a finger 19. The lancet 14 of the present disclosure consistently delivers correct lancing depth and a pre-defined lancing location, thus ensuring a sufficient sample volume.

Figure 29:
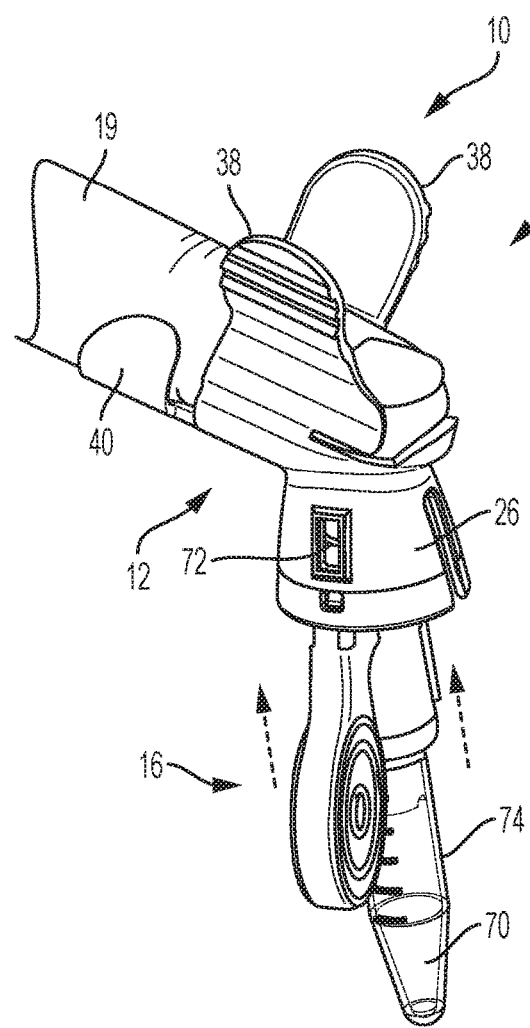
FIG. 29 is a perspective view of a third step of using a device having discrete components of the present disclosure in accordance with another embodiment of the present invention.

After the finger 19 is lanced to create blood 18 (FIG. 30) flow from the finger 19, the lancet 14 is removed from the holder 12 and the collection container 16 is pushed into the port 26 of the holder 12. Referring to FIG. 29, the container 16 is pushed into the port 26 of the holder 12 such that the container engagement portion 72 of the container 16 is locked within the locking portion 32 of the holder 12. In this manner, the container 16 is securely connected and locked to the holder 12 such that a blood sample 18 can safely flow from the finger 19 within the holder 12 to the collection cavity 70 of the container 16.

Figure 30:
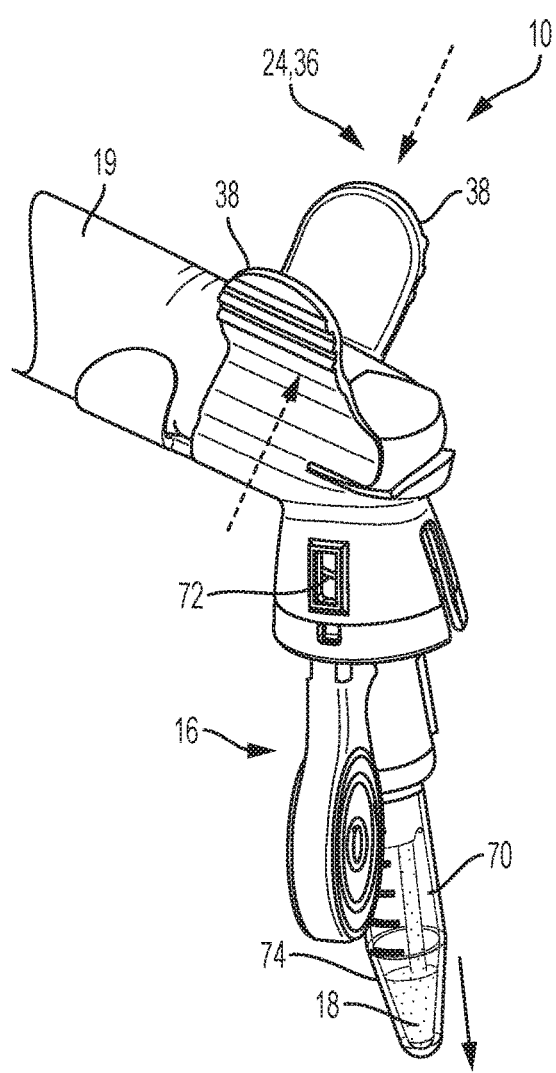
FIG. 30 is a perspective view of a fourth step of using a device having discrete components of the present disclosure in accordance with another embodiment of the present invention.

Referring to FIGS. 29 and 30, with the container 16 properly secured to the holder 12 for collection of a blood sample 18, a user is able to repeatedly squeeze and release the wings 38 of the holder 12 to pump and/or extract blood 18 from a finger 19 until a desired amount of blood 18 is filled in a collection container 16. Advantageously, with the holder 12 placed onto a finger 19, the holder 12 does not constrict the blood flow and defines lancing and finger squeezing locations. The squeezing tabs or wings 38 provide a pre-defined range of squeezing pressure that is consistently applied throughout a finger 19. By doing so, the holder 12 provides a gentle controlled finger 19 massage that stimulates blood extraction and minimizes any potential hemolysis.

For example, referring to FIGS. 2 and 3, in one embodiment, the actuation portion 24 includes a contact member 34. Referring to FIG. 2, with the actuation portion 24 in the first position, the contact member 34 is in a disengaged position, i.e., the contact member 34 is in the first position with respect to the sample source, e.g., the finger 19. Referring to FIG. 3, with the actuation portion 24 in the second position, the contact member 34 is in an engaged position, i.e., the contact member 34 is in the second position and in applied pressure contact with a sample source, e.g., the finger 19, and the actuation portion 24 of the holder 12 is able to pump and/or extract blood 18. For example, with the contact member 34 in the engaged position, the contact member 34 exerts a pressure on the sample source.

Figure 31:
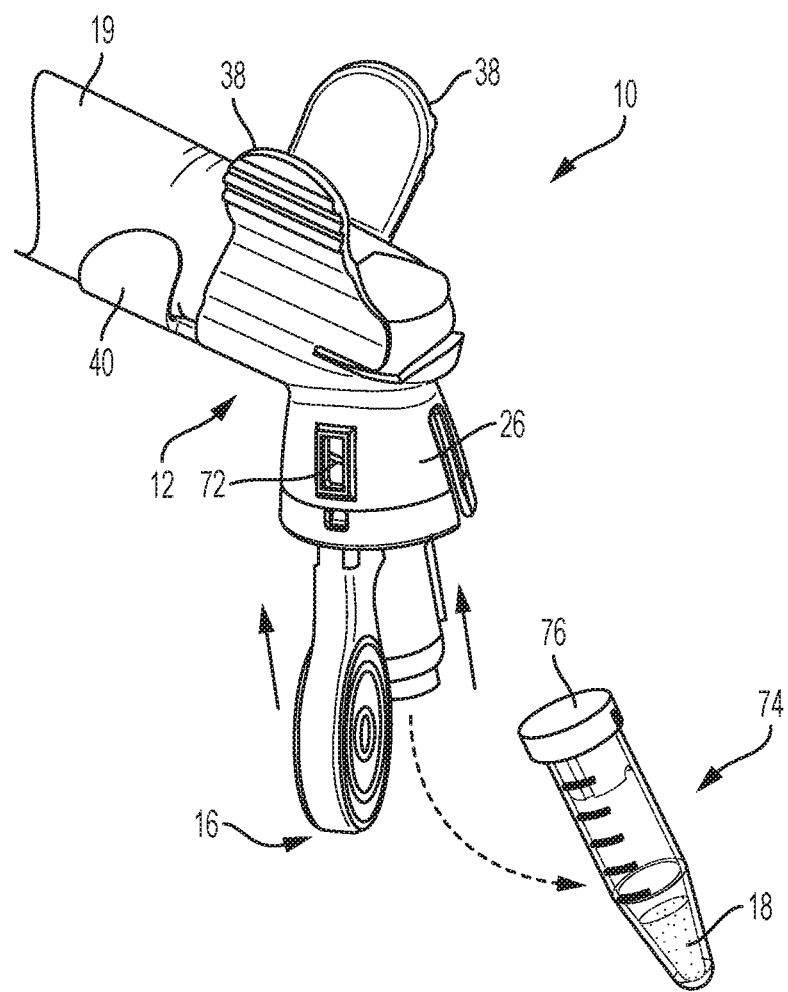
FIG. 31 is a perspective view of a fifth step of using a device having discrete components of the present disclosure in accordance with another embodiment of the present invention.

Referring to FIG. 31, once a desired amount of blood 18 is collected within the container 16, a blood collector portion 74 is detached from the collection device 10 in order to send a collected sample 18 to a diagnostic instrument and/or testing device. The blood collector portion 74 is sealed via the cap or septum 76 once removed from the collection device 10 to protectively seal the blood sample 18 within the collection cavity 70.

The devices of the present disclosure are compatible with any known testing device, whether the testing device is off-site or a point-of-care testing device. Various point-of-care testing devices are known in the art. Such point-of-care testing devices include test strips, glass slides, diagnostic cartridges, or other testing devices for testing and analysis. Test strips, glass slides, and diagnostic cartridges are point-of-care testing devices that receive a blood sample and test that blood for one or more physiological and biochemical states. There are many point-of-care devices that use cartridge based architecture to analyze very small amounts of blood bedside without the need to send the sample to a lab for analysis. This saves time in getting results over the long run, but creates a different set of challenges versus the highly routine lab environment. Examples of such testing cartridges include the i-STAT® testing cartridge from the Abbot group of companies. Testing cartridges such as the i-STAT® cartridges may be used to test for a variety of conditions including the presence of chemicals and electrolytes, hematology, blood gas concentrations, coagulation, or cardiac markers. The results of tests using such cartridges are quickly provided to the clinician.

The collection container 16 may also contain a sample stabilizer, e.g., an anticoagulant, to stabilize a blood sample and/or a component of a blood sample disposed therein. The collection container 16 may also include at least one fill line(s) corresponding to a predetermined volume of sample. The collection container may also indicate/meter a collected volume of blood.

Referring to FIGS. 17-19, in another exemplary embodiment, a device 100 for obtaining a blood sample 18 of the present disclosure has an at-angle flow and includes an integrated holder 12, lancet housing 14, and collection container 16. In such an embodiment, a user does not have to connect a separate lancet housing 14 to the port 26 of the holder 12, remove the lancet 14 after lancing the skin of a finger 19, and then connect a collection container 16 to the port 26 of the holder 12.

Referring to FIGS. 17-19, the lancet housing 14 is permanently secured within the port 26 of the holder 12. The lancet housing 14 includes a blood flow channel 120. The collection container 16 is secured to the lancet housing 14 and includes a blood collector portion 74 that is removably connectable to a portion of the lancet housing 14.

Referring to FIG. 19, in one embodiment, with the container 16 connected to the lancet housing 14, the longitudinal axis 102 of the lancet housing 14 is at an angle to the longitudinal axis 104 of the container 16. Referring to FIG. 19, in one embodiment, the lancet housing 14 is used to lance the skin of a finger 19 along a lance path 103 and then a blood sample 18 flows down a blood flow path 105 at an angle to the lance path 103.

Referring to FIGS. 17-19, in one embodiment, the device 100 includes a capillary tube 110. Referring to FIG. 19, with the container 16, i.e., the blood collector portion 74, connected to the lancet housing 14, the capillary tube 110 is in fluid communication with the inlet or opening 50 of the lancet housing 14 and the collection cavity 70 of the container 16. In one embodiment, a portion of the capillary tube 110 extends through the blood flow channel 120 of the lancet housing 14.

Referring to FIGS. 17-19, the blood flow path 105 of device 100 will now be described. With a finger 19 received within the holder 12 and the puncturing element 54 in the puncturing position, the puncturing element 54 lances the finger 19 to draw a blood sample 18. For example, when it is desired to activate the lancet 14 to lance the skin of a finger 19, the lancet 14 is pushed against a finger 19 to activate a retractable mechanism 58 of the lancet 14 to lance a finger 19. The lancet 14 of the present disclosure consistently delivers correct lancing depth and a pre-defined lancing location, thus ensuring a sufficient sample volume.

The blood 18 will flow from the finger 19 to the blood flow channel 120 of the lancet housing 14. The blood 18 flows, via blood flow path 105, at an angle to the lance path 103. For example, the blood sample 18 flows through the capillary tube 110 to the collection cavity 70 of the container 16.

Referring to FIGS. 20-22, in another exemplary embodiment, a device 200 for obtaining a blood sample 18 of the present disclosure has an in-line flow and includes an integrated holder 12, lancet housing 14, and collection container 16. In such an embodiment, a user does not have to connect a separate lancet housing 14 to the port 26 of the holder 12, remove the lancet 14 after lancing the skin of a finger 19, and then connect a collection container 16 to the port 26 of the holder 12.

Referring to FIGS. 20-22, the lancet housing 14 is permanently secured within the port 26 of the holder 12. The lancet housing 14 includes a hollow needle 62. For example, the puncturing element 54 of the lancet 14 comprises a hollow needle 62. The collection container 16 is secured to the lancet housing 14 and includes a blood collector portion 74 that is removably connectable to a portion of the lancet housing 14.

Referring to FIG. 21, in one embodiment, with the container 16 connected to the lancet housing 14, a longitudinal axis 202 of the port 26, the lancet housing 14, and the container 16 are aligned.

Referring to FIGS. 21 and 22, in one embodiment, the lancet 14 includes a hollow needle 62. In such an embodiment, the lancet housing 14 of the present disclosure is used to lance the skin of a finger 19 along a lance path 203 and then a blood sample 18 flows along a parallel blood flow path 205 through the hollow needle 62.

Referring to FIGS. 20-22, in one embodiment, the lancet housing 14 includes an outlet 210. With the container 16 connected to the lancet housing 14, the outlet 210 of the lancet housing 14 is in fluid communication with the collection cavity 70 of the container 16.

Referring to FIGS. 20-22, the blood flow path 205 of device 200 will now be described. With a finger 19 received within the holder 12 and the puncturing element 54 in the puncturing position, the puncturing element 54 lances the finger 19 to draw a blood sample 18. For example, when it is desired to activate the lancet 14 to lance the skin of a finger 19, the lancet 14 is pushed against a finger 19 to activate a retractable mechanism 58 of the lancet 14 to lance a finger 19. The lancet 14 of the present disclosure consistently delivers correct lancing depth and a pre-defined lancing location, thus ensuring a sufficient sample volume.

The blood 18 will flow from the finger 19 through the hollow needle 62 to the outlet 210 of the lancet housing 14 to the collection cavity 70 of the container 16. The blood 18 flows, via blood flow path 205, in line with the lance path 203.

Referring to FIGS. 23-26, use of a device 200 of the present disclosure having an in-line flow and including an integrated holder 12, lancet housing 14, and collection container 16, will now be described.

Figure 23:
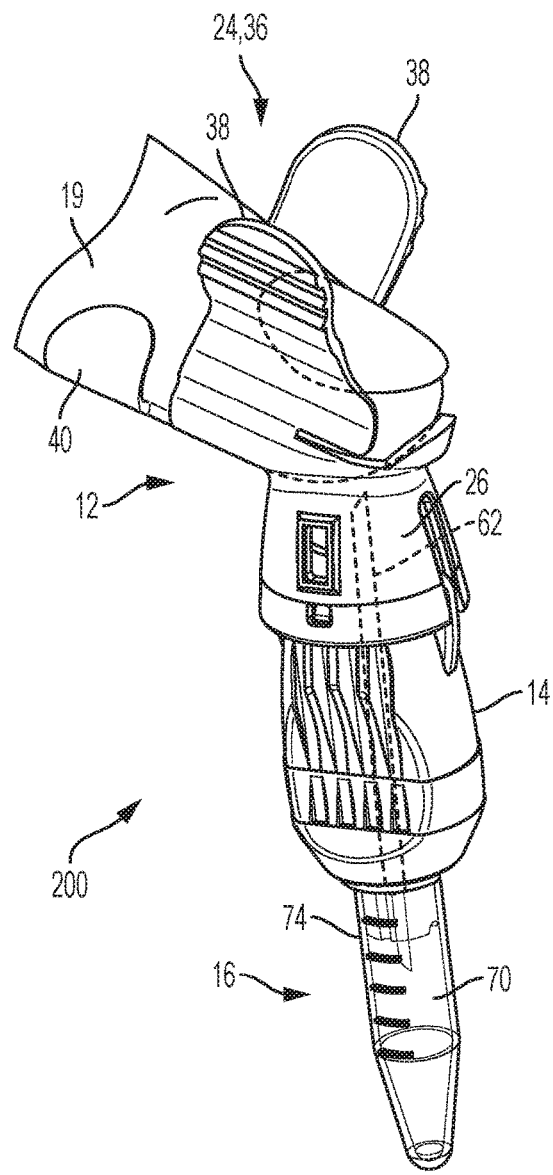
FIG. 23 is a perspective view of a first step of using an integrated device of the present disclosure in accordance with an embodiment of the present invention.

Referring to FIG. 23, first a desired finger 19 is cleaned and a holder 12 having an appropriate size for the desired finger 19 is selected and placed onto the finger 19 securely. In the integrated device 200 of the present disclosure, a separate lancet 14 and container 16 do not need to be selected and connected to the port 26 of the holder 12 as each of the holder 12, lancet housing 14, and collection container 16 are integrated into a single component.

Figure 24:
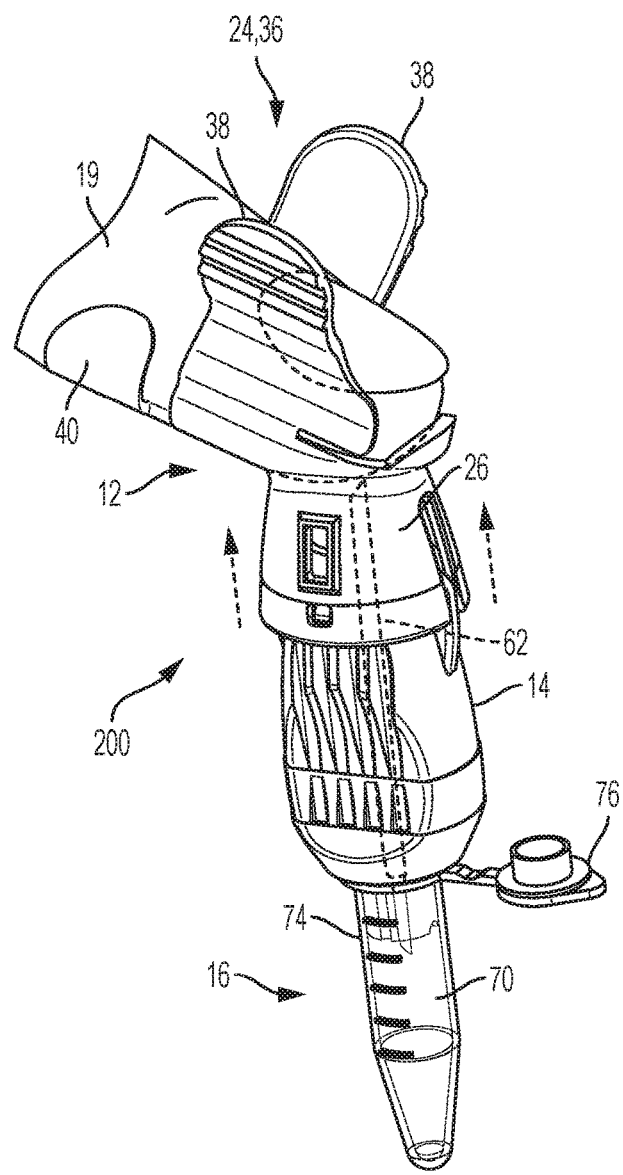
FIG. 24 is a perspective view of a second step of using an integrated device of the present disclosure in accordance with an embodiment of the present invention.

Referring to FIG. 24, when it is desired to activate the lancet 14 to lance the skin of a finger 19, the lancet 14 is pushed against a finger 19 to activate a retractable mechanism 58 (FIG. 21) of the lancet 14 to lance a finger 19. The lancet 14 of the present disclosure consistently delivers correct lancing depth and a pre-defined lancing location, thus ensuring a sufficient sample volume.

Referring to FIG. 25, after the finger 19 is lanced to create blood 18 flow from the finger 19, a user is able to repeatedly squeeze and release the wings 38 of the holder 12 to pump and/or extract blood 18 from a finger 19 until a desired amount of blood 18 is filled in a collection container 16. Advantageously, with the holder 12 placed onto a finger 19, the holder 12 does not constrict the blood flow and defines lancing and finger squeezing locations. The squeezing tabs or wings 38 provide a pre-defined range of squeezing pressure that is consistently applied throughout a finger 19. By doing so, the holder 12 provides a gentle controlled finger 19 massage that stimulates blood 18 extraction and minimizes any potential hemolysis.

Referring to FIG. 26, once a desired amount of blood 18 is collected within the container 16, a blood collector portion 74 is detached from the collection device 200 and sealed with cap or septum 76 to send a collected sample 18 to a diagnostic instrument and/or testing device. As discussed above, the collection container 16 may also contain a sample stabilizer, e.g., an anticoagulant, to stabilize blood and fill lines to indicate/meter a collected volume of blood 18.

Referring to FIGS. 11-16, use of a device 300 (FIGS. 11-13) having an at-angle flow and including an integrated lancet housing 14 and collection container 302 which can be connected with a separate holder 12; and a device 400 (FIGS. 14-16) having an in-line flow and including an integrated lancet housing 14 and collection container 402 which can be connected with a separate holder 12 will now be described.

Referring to FIGS. 11-13, the semi-integrated device 300 is used in a similar manner as the device 100 having an at-angle flow and including an integrated holder, lancet housing, and collection container described above with reference to FIGS. 17-19. With use of the semi-integrated device 300, a user does not have to connect a separate lancet housing 14 to the port 26 of the holder 12, remove the lancet 14 after lancing the skin of a finger 19, and then connect a collection container 16 to the port 26 of the holder 12. In the embodiment shown in FIGS. 11-13, a user only needs to connect an integrated lancet housing and collection container component 302 to the port 26 of the holder 12.

Referring to FIGS. 14-16, the semi-integrated device 400 is used in a similar manner as the device 200 having an in-line flow and including an integrated holder, lancet housing, and collection container described above with reference to FIGS. 20-22. With use of the semi-integrated device 400, a user does not have to connect a separate lancet housing 14 to the port 26 of the holder 12, remove the lancet 14 after lancing the skin of a finger 19, and then connect a collection container 16 to the port 26 of the holder 12. In the embodiment shown in FIGS. 14-16, a user only needs to connect an integrated lancet housing and collection container component 402 to the port 26 of the holder 12.

Any of the devices for obtaining a blood sample of the present disclosure can be used as a self-standing disposable device and/or in association with an external power source for pain reduction control. For example, a portion of holder 12 may include embedded electrodes which receive a signal from an external pain control module to deliver at least one of heat, vibration, or transcutaneous electrical nerve stimulation (TENS) for pain reduction control. The devices for obtaining a blood sample of the present disclosure may also include various options for on-board plasma separation. The devices for obtaining a blood sample of the present disclosure may also include a unique sample identifier that can be paired with patient information at the time of collection. The devices for obtaining a blood sample of the present disclosure may also include on-board diagnostic feedback at the time of collection. A device for obtaining a blood sample of the present disclosure may also allow for dual collection, e.g., the collection of two samples into two separate containers, using multiple collection ports which enable the collection of multiple samples from the same source and treating the samples with different sample stabilizers, such as anticoagulants.

A device for obtaining a blood sample of the present disclosure significantly simplifies and de-skills large volume capillary collection from a finger relative to the conventional capillary collection using lancet and capillary tube. The devices of the present disclosure eliminate blood exposure and prevents device reuse.

The devices for obtaining a blood sample of the present disclosure simplify, deskill, and streamline the collection process. This is all achieved by a self-contained closed system device which after it is placed onto a finger will provide lancing, blood extraction, stabilization and containment functions, all in one unit.

The devices for obtaining a blood sample of the present disclosure may be associated with a self-standing unit that provides automated pumping, controlled finger squeezing, and automated sample labeling and processing.

While this disclosure has been described as having exemplary designs, the present disclosure can be further modified within the spirit and scope of this disclosure. This application is therefore intended to cover any variations, uses, or adaptations of the disclosure using its general principles. Further, this application is intended to cover such departures from the present disclosure as come within known or customary practice in the art to which this disclosure pertains and which fall within the limits of the appended claims.

What is claimed is:

1. A device for obtaining a blood sample, the device comprising:
   a holder for receiving a sample source, the holder having an actuation portion and a port;
   a lancet housing secured within the port, the lancet housing having an inlet and an interior;
   a puncturing element moveable between a pre-actuated position wherein the puncturing element is retained within the interior and a puncturing position wherein at least a portion of the puncturing element extends through the inlet; and
   a container removably connectable to a portion of the lancet housing, the container defining a collection cavity,
   wherein the actuation portion is configured to be transitioned by a user between a first position in which the holder defines a first elliptical shape and a second position in which the holder defines a second elliptical shape, and
   wherein the second elliptical shape is smaller than the first elliptical shape in at least one direction.

2. The device of claim 1, wherein the actuation portion includes a contact member.

3. The device of claim 2, wherein the actuation portion is transitionable between a first position in which the contact member is in a disengaged position and a second position in which the contact member is in an engaged position.

4. The device of claim 3, wherein, with the contact member in the engaged position, the contact member exerts a pressure on the sample source.

5. The device of claim 1, wherein the actuation portion includes a pumping member for applying pressure to the sample source.

6. The device of claim 5, wherein the pumping member comprises a pair of opposed tabs.

7. The device of claim 1, wherein the sample source is a finger.

8. The device of claim 7, wherein, with the finger received within the holder, the port is in communication with a portion of the finger.

9. The device of claim 8, wherein the lancet housing includes an outlet.

10. The device of claim 9, wherein, with the container connected to the lancet housing, the outlet of the lancet housing is in fluid communication with the collection cavity of the container.

11. The device of claim 10, wherein, with the finger received within the holder and the puncturing element in the puncturing position, the puncturing element lances the finger to draw the blood sample.

12. The device of claim 11, wherein the blood sample flows through a hollow needle to the outlet to the collection cavity.

13. The device of claim 8, further comprising a capillary tube.

14. The device of claim 13, wherein, with the container connected to the lancet housing, the capillary tube is in fluid communication with the inlet of the lancet housing and the collection cavity of the container.

15. The device of claim 14, wherein, with the finger received within the holder and the puncturing element in the puncturing position, the puncturing element lances the finger to draw the blood sample.

16. The device of claim 15, wherein the blood sample flows through the capillary tube to the collection cavity.

17. The device of claim 1, wherein the puncturing element comprises a hollow needle.

18. The device of claim 1, wherein, with the container connected to the lancet housing, the longitudinal axis of the port, the lancet housing, and the container are aligned.

19. The device of claim 1, wherein, with the container connected to the lancet housing, the longitudinal axis of the lancet housing is at an angle to the longitudinal axis of the container.

20. A device for obtaining a blood sample, the device comprising:
a holder for receiving a sample source, the holder having an actuation portion and a port, wherein the actuation portion includes a pumping member for applying pressure to the sample source,
wherein the actuation portion is transitionable by a user between a first position in which the holder defines a first elliptical shape and a second position in which the holder defines a second elliptical shape, wherein the second elliptical shape is smaller than the first elliptical shape in at least one direction.

21. The device of claim 20, wherein the actuation portion includes a contact member.

22. The device of claim 21, wherein the actuation portion is transitionable between the first position in which the contact member is in a disengaged position and the second position in which the contact member is in an engaged position.

23. The device of claim 22, wherein, with the contact member in the engaged position, the contact member exerts a pressure on the sample source.

24. The device of claim 20, wherein the pumping member comprises a pair of opposed tabs.

25. The device of claim 20, wherein the sample source is a finger.

26. The device of claim 25, wherein, with the finger received within the holder, the port is in communication with a portion of the finger.

27. The device of claim 20, wherein the holder includes a stability extension portion.

28. The device of claim 20, further comprising:
a lancet housing removably connectable to the port, the lancet housing having an inlet and an interior; and
a puncturing element moveable between a pre-actuated position wherein the puncturing element is retained within the interior and a puncturing position wherein at least a portion of the puncturing element extends through the inlet.

29. The device of claim 28, further comprising a container removably connectable to the port, the container defining a collection cavity.

* * * * *